(12) United States Patent
Vidlund et al.

(10) Patent No.: US 7,666,224 B2
(45) Date of Patent: Feb. 23, 2010

(54) DEVICES AND METHODS FOR HEART VALVE TREATMENT

(75) Inventors: Robert M. Vidlund, Maplewood, MN (US); Cyril J. Schweich, Jr., Maple Grove, MN (US); Todd J. Mortier, Minneapolis, MN (US); Richard Schroeder, Fridley, MN (US); Craig Ekvall, Elk River, MN (US); Jason Kalgreen, Edina, MN (US); Edward Matthees, Minneapolis, MN (US); David Kusz, Minneapolis, MN (US)

(73) Assignee: Edwards Lifesciences LLC, Irvine, CA (US)

( * ) Notice: Subject to any disclaimer, the term of this patent is extended or adjusted under 35 U.S.C. 154(b) by 861 days.

(21) Appl. No.: 11/175,270

(22) Filed: Jul. 7, 2005

(65) Prior Publication Data

US 2006/0036317 A1 Feb. 16, 2006

Related U.S. Application Data

(63) Continuation of application No. 10/704,143, filed on Nov. 10, 2003, now Pat. No. 7,112,219.

(60) Provisional application No. 60/425,519, filed on Nov. 12, 2002.

(51) Int. Cl.
*A61F 2/24* (2006.01)
(52) U.S. Cl. .................................. 623/2.1; 623/904
(58) Field of Classification Search ....... 623/2.11–2.37, 623/904; 600/16, 37
See application file for complete search history.

(56) References Cited

U.S. PATENT DOCUMENTS 963,899 A 7/1910 Kistler (Continued)

FOREIGN PATENT DOCUMENTS

DE 32 27 984 2/1984

(Continued)

OTHER PUBLICATIONS

Edie, M.D. et al., "Surgical repair of single ventricle," *The Journal of Thoracic and Cardiovascular Surgery*, vol. 66, No. 3, Sep. 1973, pp. 350-360.

(Continued)

*Primary Examiner*—Suzette J Gherbi
(74) *Attorney, Agent, or Firm*—Finnegan, Henderson, Farabow, Garrett & Dunner, L.L.P.

(57) ABSTRACT

Devices and methods for improving the function of a valve (e.g., mitral valve) by positioning a spacing filling device outside and adjacent the heart wall such that the device applies an inward force against the heart wall acting on the valve. A substantially equal and opposite force may be provided by securing the device to the heart wall, and/or a substantially equal and opposite outward force may be applied against anatomical structure outside the heart wall. The inward force is sufficient to change the function of the valve, and may increase coaptation of the leaflets, for example. The space filling device may be implanted by a surgical approach, a transthoracic approach, or a transluminal approach, for example. The space filling portion may be delivered utilizing a delivery catheter navigated via the selected approach, and the space filling portion may be expandable between a smaller delivery configuration and a larger deployed configuration.

47 Claims, 23 Drawing Sheets

U.S. PATENT DOCUMENTS

| | | |
|---|---|---|
| 3,019,790 A | 2/1962 | Militana |
| 3,656,185 A | 4/1972 | Carpentier |
| 3,980,086 A | 9/1976 | Kletschka et al. |
| 4,035,849 A | 7/1977 | Angell et al. |
| 4,055,861 A | 11/1977 | Carpentier et al. |
| 4,192,293 A | 3/1980 | Asrican |
| 4,217,665 A | 8/1980 | Bex et al. |
| 4,261,342 A | 4/1981 | Aranguren Duo |
| 4,300,564 A | 11/1981 | Furihata |
| 4,306,319 A | 12/1981 | Kaster |
| 4,343,048 A | 8/1982 | Ross et al. |
| 4,372,293 A | 2/1983 | Vijil-Rosales |
| 4,409,974 A | 10/1983 | Freedland |
| 4,536,893 A | 8/1985 | Parravicini |
| 4,579,120 A | 4/1986 | MacGregor |
| 4,592,342 A | 6/1986 | Salmasian |
| 4,629,459 A | 12/1986 | Ionescu et al. |
| 4,632,101 A | 12/1986 | Freedland |
| 4,690,134 A | 9/1987 | Snyders |
| 4,705,040 A | 11/1987 | Mueller et al. |
| 4,936,857 A | 6/1990 | Kulik |
| 4,944,753 A | 7/1990 | Burgess et al. |
| 4,960,424 A | 10/1990 | Grooters |
| 4,991,578 A | 2/1991 | Cohen |
| 4,997,431 A | 3/1991 | Isner et al. |
| 5,061,277 A | 10/1991 | Carpentier et al. |
| 5,104,407 A | 4/1992 | Lam et al. |
| 5,106,386 A | 4/1992 | Isner et al. |
| 5,131,905 A | 7/1992 | Grooters |
| RE34,021 E | 8/1992 | Mueller et al. |
| 5,152,765 A | 10/1992 | Ross et al. |
| 5,156,621 A | 10/1992 | Navia et al. |
| 5,169,381 A | 12/1992 | Snyders |
| 5,192,314 A | 3/1993 | Daskalakis |
| 5,250,049 A | 10/1993 | Michael |
| 5,256,132 A | 10/1993 | Snyders |
| 5,258,015 A | 11/1993 | Li et al. |
| 5,284,488 A | 2/1994 | Sideris |
| 5,300,087 A | 4/1994 | Knoepfler |
| 5,312,642 A | 5/1994 | Chesterfield et al. |
| 5,360,444 A | 11/1994 | Kusuhara |
| 5,376,112 A | 12/1994 | Duren |
| 5,383,840 A | 1/1995 | Heilman et al. |
| 5,385,528 A | 1/1995 | Wilk |
| 5,389,096 A | 2/1995 | Aita et al. |
| 5,397,331 A | 3/1995 | Himpens et al. |
| 5,417,709 A | 5/1995 | Slater |
| 5,433,727 A | 7/1995 | Sideris |
| 5,445,600 A | 8/1995 | Abdulla |
| 5,450,860 A | 9/1995 | O'Connor |
| 5,452,733 A | 9/1995 | Sterman et al. |
| 5,458,574 A | 10/1995 | Machold et al. |
| 5,496,305 A | 3/1996 | Kittrell et al. |
| 5,509,428 A | 4/1996 | Dunlop |
| 5,522,884 A | 6/1996 | Wright |
| 5,533,958 A | 7/1996 | Wilk |
| 5,571,215 A | 11/1996 | Sterman et al. |
| 5,584,803 A | 12/1996 | Stevens et al. |
| 5,593,424 A | 1/1997 | Northrup, III |
| 5,607,471 A | 3/1997 | Seguin et al. |
| 5,655,548 A | 8/1997 | Nelson et al. |
| 5,665,092 A | 9/1997 | Mangiardi et al. |
| 5,674,279 A | 10/1997 | Wright et al. |
| 5,682,906 A | 11/1997 | Sterman et al. |
| 5,702,343 A | 12/1997 | Alferness |
| 5,713,954 A | 2/1998 | Rosenberg et al. |
| 5,718,725 A | 2/1998 | Sterman et al. |
| 5,738,649 A | 4/1998 | Macoviak |
| 5,755,783 A | 5/1998 | Stobie et al. |
| 5,758,663 A | 6/1998 | Wilk et al. |
| 5,766,234 A | 6/1998 | Chen et al. |
| 5,776,189 A | 7/1998 | Khalid et al. |
| 5,800,334 A | 9/1998 | Wilk |
| 5,800,528 A | 9/1998 | Lederman et al. |
| 5,800,531 A | 9/1998 | Cosgrove et al. |
| 5,807,384 A | 9/1998 | Mueller |
| 5,814,097 A | 9/1998 | Sterman et al. |
| 5,824,066 A | 10/1998 | Gross |
| 5,824,069 A | 10/1998 | Lemole |
| 5,840,059 A | 11/1998 | March et al. |
| 5,848,962 A * | 12/1998 | Feindt et al. .................. 600/16 |
| 5,849,005 A | 12/1998 | Garrison et al. |
| 5,855,601 A | 1/1999 | Bessler et al. |
| 5,855,614 A | 1/1999 | Stevens et al. |
| 5,865,791 A | 2/1999 | Whayne et al. |
| 5,876,436 A | 3/1999 | Vanney et al. |
| 5,888,240 A | 3/1999 | Carpentier et al. |
| 5,902,229 A | 5/1999 | Tsitlik et al. |
| 5,928,281 A | 7/1999 | Huynh et al. |
| 5,944,738 A | 8/1999 | Amplatz et al. |
| 5,957,977 A | 9/1999 | Melvin |
| 5,961,440 A | 10/1999 | Schweich, Jr. et al. |
| 5,961,539 A | 10/1999 | Northrup, III et al. |
| 5,961,549 A | 10/1999 | Nguyen et al. |
| 5,967,990 A | 10/1999 | Thierman et al. |
| 5,971,910 A | 10/1999 | Tsitlik et al. |
| 5,971,911 A | 10/1999 | Wilk |
| 5,972,022 A | 10/1999 | Huxel |
| 5,972,030 A | 10/1999 | Garrison et al. |
| 5,984,857 A | 11/1999 | Buck et al. |
| 5,984,917 A | 11/1999 | Fleischman et al. |
| 5,999,678 A | 12/1999 | Murphy-Chutorian et al. |
| 6,001,126 A | 12/1999 | Nguyen-Thien-Nhon |
| 6,019,722 A | 2/2000 | Spence et al. |
| 6,024,096 A | 2/2000 | Buckberg |
| 6,024,756 A | 2/2000 | Huebsch et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,071,303 A | 6/2000 | Laufer |
| 6,077,214 A | 6/2000 | Mortier et al. |
| 6,077,218 A | 6/2000 | Alferness |
| 6,079,414 A | 6/2000 | Roth |
| 6,085,754 A | 7/2000 | Alferness et al. |
| 6,086,532 A | 7/2000 | Panescu et al. |
| 6,095,968 A | 8/2000 | Snyders |
| 6,102,944 A | 8/2000 | Huynh et al. |
| 6,110,100 A | 8/2000 | Talpade |
| 6,113,536 A | 9/2000 | Aboul-Hosn et al. |
| 6,113,636 A | 9/2000 | Ogle |
| 6,117,159 A | 9/2000 | Huebsch et al. |
| 6,120,520 A | 9/2000 | Saadat et al. |
| 6,123,662 A | 9/2000 | Alferness et al. |
| 6,125,852 A | 10/2000 | Stevens et al. |
| 6,126,590 A | 10/2000 | Alferness |
| 6,129,758 A | 10/2000 | Love |
| 6,132,438 A | 10/2000 | Fleischman et al. |
| 6,143,025 A | 11/2000 | Stobie et al. |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,165,183 A | 12/2000 | Kuehn et al. |
| 6,169,922 B1 | 1/2001 | Alferness et al. |
| 6,174,279 B1 | 1/2001 | Girard |
| 6,174,332 B1 | 1/2001 | Loch et al. |
| 6,179,791 B1 | 1/2001 | Krueger |
| 6,182,664 B1 | 2/2001 | Cosgrove |
| 6,183,411 B1 | 2/2001 | Mortier et al. |
| 6,183,512 B1 | 2/2001 | Howanec, Jr. et al. |
| 6,190,408 B1 | 2/2001 | Malvin |

| Patent No. | Date | Inventor |
|---|---|---|
| 6,193,648 B1 | 2/2001 | Krueger |
| 6,197,053 B1 | 3/2001 | Cosgrove et al. |
| 6,206,004 B1 | 3/2001 | Schmidt et al. |
| 6,206,820 B1 * | 3/2001 | Kazi et al. ............... 600/16 |
| 6,210,432 B1 | 4/2001 | Solem et al. |
| 6,217,610 B1 | 4/2001 | Carpentier et al. |
| 6,221,013 B1 | 4/2001 | Panescu et al. |
| 6,221,103 B1 | 4/2001 | Melvin |
| 6,221,104 B1 | 4/2001 | Buckberg et al. |
| 6,224,540 B1 | 5/2001 | Lederman et al. |
| 6,230,714 B1 | 5/2001 | Alferness et al. |
| 6,231,518 B1 | 5/2001 | Grabek et al. |
| 6,231,561 B1 | 5/2001 | Frazier et al. |
| 6,231,602 B1 | 5/2001 | Carpentier et al. |
| 6,238,334 B1 | 5/2001 | Easterbrook, III et al. |
| 6,241,654 B1 | 6/2001 | Alferness |
| 6,245,102 B1 | 6/2001 | Jayaraman |
| 6,245,105 B1 | 6/2001 | Nguyen et al. |
| 6,250,308 B1 | 6/2001 | Cox |
| 6,251,061 B1 | 6/2001 | Hastings et al. |
| 6,258,021 B1 | 7/2001 | Wilk |
| 6,258,023 B1 | 7/2001 | Rogers et al. |
| 6,260,552 B1 | 7/2001 | Mortier et al. |
| 6,260,820 B1 | 7/2001 | Chowdhury |
| 6,261,222 B1 | 7/2001 | Schweich, Jr. et al. |
| 6,264,602 B1 | 7/2001 | Mortier et al. |
| 6,269,819 B1 | 8/2001 | Oz et al. |
| 6,283,993 B1 | 9/2001 | Cosgrove et al. |
| 6,290,674 B1 | 9/2001 | Roue et al. |
| 6,293,906 B1 | 9/2001 | Vanden Hoek et al. |
| 6,309,370 B1 | 10/2001 | Haim et al. |
| 6,312,447 B1 | 11/2001 | Grimes |
| 6,314,322 B1 | 11/2001 | Rosenberg |
| 6,328,727 B1 | 12/2001 | Frazier et al. |
| 6,331,157 B2 | 12/2001 | Hancock |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,338,712 B2 | 1/2002 | Spence et al. |
| 6,343,605 B1 | 2/2002 | Lafontaine |
| 6,360,749 B1 | 3/2002 | Jayaraman |
| 6,361,545 B1 | 3/2002 | Macoviak et al. |
| 6,370,429 B1 | 4/2002 | Alferness et al. |
| 6,375,608 B1 | 4/2002 | Alferness |
| 6,379,366 B1 | 4/2002 | Fleischman et al. |
| 6,402,679 B1 * | 6/2002 | Mortier et al. ............. 600/16 |
| 6,402,680 B2 | 6/2002 | Mortier et al. |
| 6,402,781 B1 | 6/2002 | Langberg et al. |
| 6,406,420 B1 | 6/2002 | McCarthy et al. |
| 6,406,422 B1 | 6/2002 | Landesberg |
| 6,409,759 B1 | 6/2002 | Peredo |
| 6,409,760 B1 | 6/2002 | Melvin |
| 6,416,459 B1 | 7/2002 | Haindl |
| 6,419,669 B1 | 7/2002 | Frazier et al. |
| 6,423,051 B1 | 7/2002 | Kaplan et al. |
| 6,425,856 B1 | 7/2002 | Shapland et al. |
| 6,432,039 B1 | 8/2002 | Wardle |
| 6,432,059 B2 | 8/2002 | Hickey |
| 6,436,088 B2 | 8/2002 | Frazier et al. |
| 6,439,237 B1 | 8/2002 | Buckberg et al. |
| 6,443,949 B2 | 9/2002 | Altman |
| 6,450,171 B1 | 9/2002 | Buckberg et al. |
| 6,458,100 B2 | 10/2002 | Roue et al. |
| 6,461,366 B1 | 10/2002 | Seguin |
| 6,478,729 B1 | 11/2002 | Rogers et al. |
| 6,482,146 B1 | 11/2002 | Alferness et al. |
| 6,488,706 B1 | 12/2002 | Solymar |
| 6,494,825 B1 | 12/2002 | Talpade |
| 6,508,756 B1 | 1/2003 | Kung et al. |
| 6,511,426 B1 | 1/2003 | Hossack et al. |
| 6,514,194 B2 | 2/2003 | Schweich, Jr. et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,537,314 B2 | 3/2003 | Langberg et al. |
| 6,544,167 B2 | 4/2003 | Buckberg et al. |
| 6,544,180 B1 | 4/2003 | Doten et al. |
| 6,547,821 B1 | 4/2003 | Taylor et al. |
| 6,569,198 B1 | 5/2003 | Wilson et al. |
| 6,572,529 B2 | 6/2003 | Wilk |
| 6,582,355 B2 | 6/2003 | Alferness et al. |
| 6,587,734 B2 | 7/2003 | Okuzumi |
| 6,589,160 B2 | 7/2003 | Schweich, Jr. et al. |
| 6,592,619 B2 | 7/2003 | Melvin |
| 6,595,912 B2 | 7/2003 | Lau et al. |
| 6,602,182 B1 | 8/2003 | Milbocker |
| 6,602,184 B2 | 8/2003 | Lau et al. |
| 6,612,278 B2 | 9/2003 | Kampichler |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,619,291 B2 | 9/2003 | Hlavka |
| 6,622,730 B2 | 9/2003 | Ekvall et al. |
| 6,626,821 B1 | 9/2003 | Kung et al. |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,645,139 B2 | 11/2003 | Haindl |
| 6,651,671 B1 | 11/2003 | Donlon et al. |
| 6,656,221 B2 | 12/2003 | Taylor et al. |
| 6,663,558 B2 | 12/2003 | Lau et al. |
| 6,669,708 B1 | 12/2003 | Nissenbaum et al. |
| 6,673,009 B1 | 1/2004 | Vanden Hoek et al. |
| 6,676,702 B2 | 1/2004 | Mathis |
| 6,681,773 B2 | 1/2004 | Murphy et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,685,646 B2 | 2/2004 | Cespedes et al. |
| 6,689,048 B2 | 2/2004 | Vanden Hoek et al. |
| 6,695,768 B1 | 2/2004 | Levine et al. |
| 6,695,866 B1 | 2/2004 | Kuehn et al. |
| 6,701,929 B2 * | 3/2004 | Hussein ............... 128/898 |
| 6,702,732 B1 | 3/2004 | Lau et al. |
| 6,702,763 B2 | 3/2004 | Murphy et al. |
| 6,702,826 B2 | 3/2004 | Liddicoat et al. |
| 6,706,065 B2 | 3/2004 | Langberg et al. |
| 6,709,456 B2 | 3/2004 | Langberg et al. |
| 6,712,804 B2 | 3/2004 | Roue et al. |
| 6,716,158 B2 | 4/2004 | Raman et al. |
| 6,719,767 B1 | 4/2004 | Kimblad |
| 6,723,038 B1 * | 4/2004 | Schroeder et al. ............. 600/16 |
| 6,726,716 B2 | 4/2004 | Marquez |
| 6,726,717 B2 | 4/2004 | Alfieri et al. |
| 6,730,016 B1 | 5/2004 | Cox et al. |
| 6,733,525 B2 | 5/2004 | Yang et al. |
| 6,740,107 B2 | 5/2004 | Loeb et al. |
| 6,752,813 B2 | 6/2004 | Goldfarb et al. |
| 6,755,777 B2 | 6/2004 | Schweich, Jr. et al. |
| 6,755,779 B2 | 6/2004 | Vanden Hoek et al. |
| 6,767,362 B2 | 7/2004 | Schreck |
| 6,769,434 B2 | 8/2004 | Liddicoat et al. |
| 6,776,754 B1 | 8/2004 | Wilk |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,805,710 B2 | 10/2004 | Bolling et al. |
| 6,810,882 B2 | 11/2004 | Langberg et al. |
| 6,814,700 B1 | 11/2004 | Mueller et al. |
| 6,824,562 B2 | 11/2004 | Mathis et al. |
| 6,830,585 B1 | 12/2004 | Artof et al. |
| 6,837,247 B2 | 1/2005 | Buckberg et al. |

| | | |
|---|---|---|
| 6,846,296 B1 | 1/2005 | Millbocker et al. |
| 6,858,039 B2 | 2/2005 | McCarthy |
| 6,875,224 B2 | 4/2005 | Grimes |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,890,353 B2 | 5/2005 | Cohn et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,908,426 B2 | 6/2005 | Shapland et al. |
| 6,908,478 B2 | 6/2005 | Alferness et al. |
| 6,913,608 B2 | 7/2005 | Liddicoat et al. |
| 6,918,917 B1 | 7/2005 | Nguyen et al. |
| 6,921,407 B2 | 7/2005 | Nguyen et al. |
| 6,949,122 B2 | 9/2005 | Adams et al. |
| 6,951,534 B2 | 10/2005 | Girard et al. |
| 6,955,689 B2 | 10/2005 | Ryan et al. |
| 6,959,711 B2 | 11/2005 | Murphy et al. |
| 6,960,229 B2 | 11/2005 | Mathis et al. |
| 6,962,605 B2 | 11/2005 | Cosgrove et al. |
| 6,966,926 B2 | 11/2005 | Mathis |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,994,093 B2 | 2/2006 | Murphy et al. |
| 6,997,865 B2 | 2/2006 | Alferness et al. |
| 6,997,950 B2 | 2/2006 | Chawla |
| 6,997,951 B2 | 2/2006 | Solem et al. |
| 7,004,958 B2 | 2/2006 | Adams et al. |
| 7,011,682 B2 | 3/2006 | Lashinski et al. |
| 7,022,064 B2 | 4/2006 | Alferness et al. |
| 7,025,719 B2 | 4/2006 | Alferness et al. |
| 7,037,334 B1 | 5/2006 | Hlavka et al. |
| 7,044,967 B1 | 5/2006 | Solem et al. |
| 7,052,487 B2 | 5/2006 | Cohn et al. |
| 7,056,280 B2 | 6/2006 | Buckberg et al. |
| 7,060,021 B1 | 6/2006 | Wilk |
| 7,063,722 B2 | 6/2006 | Marquez |
| 7,070,618 B2 | 7/2006 | Streeter |
| 7,083,628 B2 | 8/2006 | Bachman |
| 7,087,064 B1 | 8/2006 | Hyde |
| 7,090,695 B2 | 8/2006 | Solem et al. |
| 7,112,207 B2 | 9/2006 | Allen et al. |
| 7,112,219 B2 | 9/2006 | Vidlund et al. |
| 7,115,110 B2 | 10/2006 | Frazier et al. |
| 7,125,420 B2 | 10/2006 | Rourke et al. |
| 7,153,258 B2 | 12/2006 | Alferness et al. |
| 7,163,507 B2 | 1/2007 | Alferness |
| 7,166,071 B2 | 1/2007 | Alferness |
| 7,166,126 B2 | 1/2007 | Spence et al. |
| 7,179,282 B2 | 2/2007 | Alferness et al. |
| 7,186,264 B2 | 3/2007 | Liddicoat et al. |
| 7,189,199 B2 | 3/2007 | McCarthy et al. |
| 7,192,442 B2 | 3/2007 | Solem et al. |
| 7,214,181 B2 | 5/2007 | Shapland et al. |
| 7,220,277 B2 | 5/2007 | Arru et al. |
| 7,226,467 B2 | 6/2007 | Lucatero et al. |
| 7,226,477 B2 | 6/2007 | Cox |
| 7,229,469 B1 | 6/2007 | Witzel et al. |
| 7,241,310 B2 | 7/2007 | Taylor et al. |
| 7,247,134 B2 | 7/2007 | Vidlund et al. |
| 7,252,632 B2 | 8/2007 | Shapland et al. |
| 7,255,674 B2 | 8/2007 | Alferness |
| 7,261,684 B2 | 8/2007 | Alferness |
| 7,264,587 B2 | 9/2007 | Chin |
| 7,270,676 B2 | 9/2007 | Alferness et al. |
| 7,275,546 B2 | 10/2007 | Buckberg et al. |
| 7,276,078 B2 | 10/2007 | Spenser et al. |
| 7,278,964 B2 | 10/2007 | Alferness |
| 7,291,168 B2 | 11/2007 | Macoviak et al. |
| 7,296,577 B2 | 11/2007 | Lashinski et al. |
| 7,309,354 B2 | 12/2007 | Mathis et al. |
| 7,311,728 B2 | 12/2007 | Solem et al. |
| 7,311,729 B2 | 12/2007 | Mathis et al. |
| 7,311,731 B2 | 12/2007 | Lesniak et al. |
| 7,326,174 B2 | 2/2008 | Cox et al. |
| 7,329,280 B2 | 2/2008 | Bolling et al. |
| 7,335,213 B1 | 2/2008 | Hyde et al. |
| 7,351,200 B2 | 4/2008 | Alferness |
| 7,361,137 B2 | 4/2008 | Taylor et al. |
| 7,364,588 B2 | 4/2008 | Mathis et al. |
| 7,373,207 B2 | 5/2008 | Lattouf |
| 7,377,940 B2 | 5/2008 | Ryan et al. |
| 7,381,182 B2 | 6/2008 | Raman et al. |
| 7,381,220 B2 | 6/2008 | Macoviak et al. |
| 7,390,293 B2 | 6/2008 | Jayaraman |
| 7,410,461 B2 | 8/2008 | Lau et al. |
| 7,419,466 B2 | 9/2008 | Vanden Hoek et al. |
| 2001/0003986 A1 | 6/2001 | Cosgrove |
| 2001/0005787 A1 | 6/2001 | Oz et al. |
| 2001/0009976 A1 | 7/2001 | Panescu et al. |
| 2001/0014800 A1 | 8/2001 | Frazier et al. |
| 2001/0014811 A1 | 8/2001 | Hussein |
| 2001/0018611 A1 | 8/2001 | Solem et al. |
| 2001/0021874 A1 | 9/2001 | Carpentier et al. |
| 2001/0029314 A1 | 10/2001 | Alferness et al. |
| 2001/0034551 A1 | 10/2001 | Cox |
| 2001/0037123 A1 | 11/2001 | Hancock |
| 2001/0039434 A1 | 11/2001 | Frazier et al. |
| 2001/0039435 A1 | 11/2001 | Roue et al. |
| 2001/0039436 A1 | 11/2001 | Frazier et al. |
| 2001/0041821 A1 | 11/2001 | Wilk |
| 2001/0041914 A1 | 11/2001 | Frazier et al. |
| 2001/0041915 A1 | 11/2001 | Roue et al. |
| 2001/0044568 A1 | 11/2001 | Langberg et al. |
| 2001/0047122 A1 | 11/2001 | Vanden Hoek et al. |
| 2001/0049492 A1 | 12/2001 | Frazier et al. |
| 2002/0007216 A1 | 1/2002 | Melvin |
| 2002/0013571 A1 | 1/2002 | Goldfarb et al. |
| 2002/0016628 A1 | 2/2002 | Langberg et al. |
| 2002/0019580 A1 | 2/2002 | Lau et al. |
| 2002/0022880 A1 | 2/2002 | Melvin |
| 2002/0026092 A1 | 2/2002 | Buckberg et al. |
| 2002/0026094 A1 | 2/2002 | Roth |
| 2002/0028981 A1 | 3/2002 | Lau et al. |
| 2002/0029783 A1 | 3/2002 | Stevens et al. |
| 2002/0032364 A1 | 3/2002 | Lau et al. |
| 2002/0042554 A1 | 4/2002 | Alferness et al. |
| 2002/0045798 A1 | 4/2002 | Lau et al. |
| 2002/0045799 A1 | 4/2002 | Lau et al. |
| 2002/0045800 A1 | 4/2002 | Lau et al. |
| 2002/0052538 A1 | 5/2002 | Lau et al. |
| 2002/0056461 A1 | 5/2002 | Jayaraman |
| 2002/0058855 A1 | 5/2002 | Schweich, Jr. et al. |
| 2002/0065449 A1 | 5/2002 | Wardle |
| 2002/0065465 A1 | 5/2002 | Panescu et al. |
| 2002/0065554 A1 | 5/2002 | Streeter |
| 2002/0068850 A1 | 6/2002 | Vanden Hoek et al. |
| 2002/0077532 A1 | 6/2002 | Gannoe et al. |
| 2002/0082647 A1 | 6/2002 | Alferness et al. |
| 2002/0087173 A1 | 7/2002 | Alferness et al. |
| 2002/0091296 A1 | 7/2002 | Alferness |
| 2002/0103511 A1 | 8/2002 | Alferness et al. |
| 2002/0103532 A1 | 8/2002 | Langberg et al. |
| 2002/0103533 A1 | 8/2002 | Langberg et al. |
| 2002/0111533 A1 | 8/2002 | Melvin |
| 2002/0111567 A1 | 8/2002 | Vanden Hoek et al. |
| 2002/0111636 A1 | 8/2002 | Fleischman et al. |
| 2002/0133055 A1 | 9/2002 | Haindl |
| 2002/0143250 A1 | 10/2002 | Panescu et al. |
| 2002/0151766 A1 | 10/2002 | Shapland et al. |
| 2002/0151961 A1 | 10/2002 | Lashinski et al. |
| 2002/0161275 A1 | 10/2002 | Schweich, Jr. et al. |
| 2002/0169358 A1 | 11/2002 | Mortier et al. |
| 2002/0169359 A1 | 11/2002 | McCarthy et al. |

| | | | | | |
|---|---|---|---|---|---|
| 2002/0169360 A1 | 11/2002 | Taylor et al. | 2004/0059188 A1 | 3/2004 | Alferness |
| 2002/0169502 A1 | 11/2002 | Mathis | 2004/0059189 A1 | 3/2004 | Alferness |
| 2002/0169504 A1 | 11/2002 | Alferness et al. | 2004/0059351 A1 | 3/2004 | Eigler et al. |
| 2002/0173694 A1 | 11/2002 | Mortier et al. | 2004/0064014 A1 | 4/2004 | Melvin et al. |
| 2002/0183835 A1 | 12/2002 | Taylor et al. | 2004/0073302 A1 | 4/2004 | Rourke et al. |
| 2002/0183836 A1 | 12/2002 | Liddicoat et al. | 2004/0092962 A1 | 5/2004 | Thornton et al. |
| 2002/0183837 A1 | 12/2002 | Streeter et al. | 2004/0093023 A1 | 5/2004 | Allen et al. |
| 2002/0183838 A1 | 12/2002 | Liddicoat et al. | 2004/0098116 A1 | 5/2004 | Callas et al. |
| 2002/0183841 A1 | 12/2002 | Cohn et al. | 2004/0102678 A1 | 5/2004 | Haindl |
| 2002/0188170 A1 | 12/2002 | Santamore et al. | 2004/0102679 A1 | 5/2004 | Alferness et al. |
| 2002/0188350 A1 | 12/2002 | Arru et al. | 2004/0102839 A1 | 5/2004 | Cohn et al. |
| 2003/0004396 A1 | 1/2003 | Vanden Hock et al. | 2004/0102840 A1 | 5/2004 | Solem et al. |
| 2003/0009081 A1 | 1/2003 | Rogers et al. | 2004/0111095 A1 | 6/2004 | Gordon et al. |
| 2003/0023132 A1 | 1/2003 | Melvin et al. | 2004/0111101 A1 | 6/2004 | Chin |
| 2003/0028077 A1 | 2/2003 | Alferness et al. | 2004/0122448 A1 | 6/2004 | Levine |
| 2003/0032979 A1 | 2/2003 | Mortier et al. | 2004/0122512 A1 | 6/2004 | Navia et al. |
| 2003/0045771 A1 | 3/2003 | Schweich, Jr. et al. | 2004/0122513 A1 | 6/2004 | Navia et al. |
| 2003/0045776 A1 | 3/2003 | Alferness et al. | 2004/0127980 A1 | 7/2004 | Kowalsky et al. |
| 2003/0045896 A1 | 3/2003 | Murphy et al. | 2004/0127981 A1 | 7/2004 | Rahdert et al. |
| 2003/0050529 A1 | 3/2003 | Vidlund et al. | 2004/0127982 A1 | 7/2004 | Machold et al. |
| 2003/0050659 A1 | 3/2003 | Murphy et al. | 2004/0127983 A1 | 7/2004 | Mortier et al. |
| 2003/0060674 A1 | 3/2003 | Gifford, III et al. | 2004/0133062 A1 | 7/2004 | Pai et al. |
| 2003/0065248 A1 | 4/2003 | Lau et al. | 2004/0133063 A1 | 7/2004 | McCarthy et al. |
| 2003/0069467 A1 | 4/2003 | Lau et al. | 2004/0133069 A1 | 7/2004 | Shapland et al. |
| 2003/0078465 A1 | 4/2003 | Pai et al. | 2004/0133220 A1 | 7/2004 | Lashinski et al. |
| 2003/0078653 A1 | 4/2003 | Vesely et al. | 2004/0133240 A1 | 7/2004 | Adams et al. |
| 2003/0078671 A1 | 4/2003 | Lesniak et al. | 2004/0133273 A1 | 7/2004 | Cox |
| 2003/0093104 A1 | 5/2003 | Bonner et al. | 2004/0138526 A1 | 7/2004 | Guenst |
| 2003/0105519 A1 | 6/2003 | Fasol et al. | 2004/0138744 A1 | 7/2004 | Lashinski et al. |
| 2003/0120340 A1 | 6/2003 | Liska et al. | 2004/0143323 A1 | 7/2004 | Chawla |
| 2003/0130730 A1 | 7/2003 | Cohn et al. | 2004/0148019 A1 | 7/2004 | Vidlund et al. |
| 2003/0130731 A1 | 7/2003 | Vidlund et al. | 2004/0148020 A1 | 7/2004 | Vidlund et al. |
| 2003/0135267 A1 | 7/2003 | Solem et al. | 2004/0152947 A1 | 8/2004 | Schroeder et al. |
| 2003/0144697 A1 | 7/2003 | Mathis et al. | 2004/0158123 A1 | 8/2004 | Jayaraman |
| 2003/0149333 A1 | 8/2003 | Alferness | 2004/0158321 A1 | 8/2004 | Reuter et al. |
| 2003/0153946 A1 | 8/2003 | Kimblad | 2004/0162610 A1 | 8/2004 | Liska et al. |
| 2003/0158570 A1 | 8/2003 | Ferrazzi | 2004/0167374 A1 | 8/2004 | Schweich et al. |
| 2003/0166992 A1 | 9/2003 | Schweich, Jr. et al. | 2004/0167539 A1 | 8/2004 | Kuehn et al. |
| 2003/0171641 A1 | 9/2003 | Schweich, Jr. et al. | 2004/0171907 A1 | 9/2004 | Alferness et al. |
| 2003/0171776 A1 | 9/2003 | Adams et al. | 2004/0171908 A1 | 9/2004 | Alferness et al. |
| 2003/0171806 A1 | 9/2003 | Mathis et al. | 2004/0171909 A1 | 9/2004 | Alferness |
| 2003/0181928 A1 | 9/2003 | Vidlund et al. | 2004/0172046 A1 | 9/2004 | Hlavka et al. |
| 2003/0191538 A1 | 10/2003 | Buckberg et al. | 2004/0176678 A1 | 9/2004 | Murphy et al. |
| 2003/0199733 A1 | 10/2003 | Shapland et al. | 2004/0176679 A1 | 9/2004 | Murphy et al. |
| 2003/0212453 A1 | 11/2003 | Mathis et al. | 2004/0176840 A1 | 9/2004 | Langberg et al. |
| 2003/0225454 A1 | 12/2003 | Mathis et al. | 2004/0181121 A1 | 9/2004 | Alferness et al. |
| 2003/0229260 A1 | 12/2003 | Girard et al. | 2004/0181122 A1 | 9/2004 | Alferness et al. |
| 2003/0229261 A1 | 12/2003 | Girard et al. | 2004/0181123 A1 | 9/2004 | Alferness et al. |
| 2003/0229265 A1 | 12/2003 | Girard et al. | 2004/0181124 A1 | 9/2004 | Alferness |
| 2003/0229266 A1 | 12/2003 | Cox et al. | 2004/0181125 A1 | 9/2004 | Alferness et al. |
| 2003/0233022 A1 | 12/2003 | Vidlund et al. | 2004/0181126 A1 | 9/2004 | Buckberg et al. |
| 2003/0233142 A1 | 12/2003 | Morales et al. | 2004/0181238 A1 | 9/2004 | Zarbatany et al. |
| 2003/0236569 A1 | 12/2003 | Mathis et al. | 2004/0186342 A1 | 9/2004 | Vanden Hock et al. |
| 2004/0002719 A1 | 1/2004 | Oz et al. | 2004/0186566 A1 | 9/2004 | Hindrichs et al. |
| 2004/0003819 A1 | 1/2004 | St. Goar et al. | 2004/0193191 A1 | 9/2004 | Starksen et al. |
| 2004/0010305 A1 | 1/2004 | Alferness et al. | 2004/0193260 A1 | 9/2004 | Alferness et al. |
| 2004/0015039 A1 | 1/2004 | Melvin | 2004/0199183 A1 | 10/2004 | Oz et al. |
| 2004/0015040 A1 | 1/2004 | Melvin | 2004/0206363 A1 | 10/2004 | McCarthy et al. |
| 2004/0015041 A1 | 1/2004 | Melvin | 2004/0210240 A1 | 10/2004 | Saint |
| 2004/0019377 A1 | 1/2004 | Taylor et al. | 2004/0210303 A1 | 10/2004 | Sedransk |
| 2004/0019378 A1 | 1/2004 | Hlavka et al. | 2004/0210304 A1 | 10/2004 | Seguin et al. |
| 2004/0024286 A1 | 2/2004 | Melvin | 2004/0210306 A1 | 10/2004 | Quijano et al. |
| 2004/0030382 A1 | 2/2004 | St. Goar et al. | 2004/0210307 A1 | 10/2004 | Khairkhahan |
| 2004/0034271 A1 | 2/2004 | Melvin et al. | 2004/0220593 A1 | 11/2004 | Greenhalgh |
| 2004/0039442 A1 | 2/2004 | St. Goar et al. | 2004/0225300 A1 | 11/2004 | Goldfarb et al. |
| 2004/0039443 A1 | 2/2004 | Solem et al. | 2004/0243227 A1 | 12/2004 | Stariksen et al. |
| 2004/0044365 A1 | 3/2004 | Bachman | 2004/0243228 A1 | 12/2004 | Kowalsky et al. |
| 2004/0049115 A1 | 3/2004 | Murphy et al. | 2004/0243229 A1 | 12/2004 | Vidlund et al. |
| 2004/0049116 A1 | 3/2004 | Murphy et al. | 2004/0249452 A1 | 12/2004 | Adams et al. |
| 2004/0059180 A1 | 3/2004 | Melvin | 2004/0254600 A1 | 12/2004 | Zarbatany et al. |
| 2004/0059181 A1 | 3/2004 | Alferness | 2004/0260317 A1 | 12/2004 | Bloom et al. |
| 2004/0059182 A1 | 3/2004 | Alferness | 2004/0260393 A1 | 12/2004 | Rahdert et al. |
| 2004/0059187 A1 | 3/2004 | Alferness | 2004/0267083 A1 | 12/2004 | McCarthy et al. |

| | | | | | |
|---|---|---|---|---|---|
| 2004/0267329 A1 | 12/2004 | Raman et al. | 2005/0222489 A1 | 10/2005 | Rahdert et al. |
| 2004/0267358 A1 | 12/2004 | Reitan | 2005/0222678 A1 | 10/2005 | Lashinski et al. |
| 2005/0004428 A1 | 1/2005 | Cox et al. | 2005/0228217 A1 | 10/2005 | Alferness et al. |
| 2005/0004665 A1 | 1/2005 | Aklog | 2005/0228422 A1 | 10/2005 | Machold et al. |
| 2005/0004666 A1 | 1/2005 | Alfieri et al. | 2005/0240200 A1 | 10/2005 | Bergheim |
| 2005/0004667 A1 | 1/2005 | Swinford et al. | 2005/0246014 A1 | 11/2005 | McCarthy |
| 2005/0004668 A1 | 1/2005 | Aklog et al. | 2005/0256567 A1 | 11/2005 | Lim et al. |
| 2005/0010240 A1 | 1/2005 | Mathis et al. | 2005/0256568 A1 | 11/2005 | Lim et al. |
| 2005/0010283 A1 | 1/2005 | Vijay | 2005/0256569 A1 | 11/2005 | Lim et al. |
| 2005/0010286 A1 | 1/2005 | Vijay | 2005/0261704 A1 | 11/2005 | Mathis et al. |
| 2005/0021056 A1 | 1/2005 | St. Goar et al. | 2005/0267574 A1 | 12/2005 | Cohn et al. |
| 2005/0021057 A1 | 1/2005 | St. Goar et al. | 2005/0272969 A1 | 12/2005 | Alferness et al. |
| 2005/0021121 A1 | 1/2005 | Reuter et al. | 2005/0278022 A1 | 12/2005 | Lim |
| 2005/0021135 A1 | 1/2005 | Ryan et al. | 2006/0004443 A1 | 1/2006 | Liddicoat et al. |
| 2005/0027351 A1 | 2/2005 | Reuter et al. | 2006/0009842 A1 | 1/2006 | Huynh et al. |
| 2005/0027353 A1 | 2/2005 | Alferness et al. | 2006/0020336 A1 | 1/2006 | Liddicoat |
| 2005/0027369 A1 | 2/2005 | Eldridge et al. | 2006/0025787 A1 | 2/2006 | Morales et al. |
| 2005/0033419 A1 | 2/2005 | Alferness et al. | 2006/0025856 A1 | 2/2006 | Ryan et al. |
| 2005/0033446 A1 | 2/2005 | Deem et al. | 2006/0030866 A1 | 2/2006 | Schreck |
| 2005/0038506 A1 | 2/2005 | Webler et al. | 2006/0030882 A1 | 2/2006 | Adams et al. |
| 2005/0038507 A1 | 2/2005 | Alferness et al. | 2006/0030885 A1 | 2/2006 | Hyde |
| 2005/0038509 A1 | 2/2005 | Ashe | 2006/0036317 A1 | 2/2006 | Vidlund et al. |
| 2005/0043792 A1 | 2/2005 | Solem et al. | 2006/0041306 A1 | 2/2006 | Vidlund et al. |
| 2005/0049679 A1 | 3/2005 | Taylor et al. | 2006/0052868 A1 | 3/2006 | Mortier et al. |
| 2005/0049698 A1 | 3/2005 | Bolling et al. | 2006/0058817 A1 | 3/2006 | Starksen et al. |
| 2005/0055087 A1 | 3/2005 | Starksen | 2006/0063970 A1 | 3/2006 | Raman et al. |
| 2005/0055089 A1 | 3/2005 | Macoviak et al. | 2006/0064115 A1 | 3/2006 | Allen et al. |
| 2005/0059854 A1 | 3/2005 | Vanden Hoek et al. | 2006/0064116 A1 | 3/2006 | Allen et al. |
| 2005/0060030 A1 | 3/2005 | Lashinski et al. | 2006/0064118 A1 | 3/2006 | Kimblad |
| 2005/0065550 A1 | 3/2005 | Starksen et al. | 2006/0069430 A9 | 3/2006 | Rahdert et al. |
| 2005/0065598 A1 | 3/2005 | Mathis et al. | 2006/0095025 A1 | 5/2006 | Levine et al. |
| 2005/0065601 A1 | 3/2005 | Lee et al. | 2006/0100699 A1 | 5/2006 | Vidlund et al. |
| 2005/0070998 A1 | 3/2005 | Rourke et al. | 2006/0106456 A9 | 5/2006 | Machold et al. |
| 2005/0071000 A1 | 3/2005 | Liddicoat et al. | 2006/0111607 A1 | 5/2006 | Alferness et al. |
| 2005/0075723 A1 | 4/2005 | Schroeder et al. | 2006/0116756 A1 | 6/2006 | Solem et al. |
| 2005/0075727 A1 | 4/2005 | Wheatley | 2006/0116757 A1 | 6/2006 | Lashinski et al. |
| 2005/0080402 A1 | 4/2005 | Santamore et al. | 2006/0129025 A1 | 6/2006 | Levine et al. |
| 2005/0080483 A1 | 4/2005 | Solem et al. | 2006/0129188 A1 | 6/2006 | Starksen et al. |
| 2005/0085688 A1 | 4/2005 | Girard et al. | 2006/0137697 A1 | 6/2006 | Murphy et al. |
| 2005/0095268 A1 | 5/2005 | Walsh et al. | 2006/0142854 A1 | 6/2006 | Alferness et al. |
| 2005/0096666 A1 | 5/2005 | Gordon et al. | 2006/0149122 A1 | 7/2006 | Shapland et al. |
| 2005/0096740 A1 | 5/2005 | Langberg et al. | 2006/0149123 A1 | 7/2006 | Vidlund et al. |
| 2005/0107810 A1 | 5/2005 | Morales et al. | 2006/0149368 A1 | 7/2006 | Spence |
| 2005/0107811 A1 | 5/2005 | Starksen et al. | 2006/0155165 A1 | 7/2006 | Vanden Hoek et al. |
| 2005/0107812 A1 | 5/2005 | Starksen et al. | 2006/0161040 A1 | 7/2006 | McCarthy et al. |
| 2005/0113635 A1 | 5/2005 | Whayne et al. | 2006/0173536 A1 | 8/2006 | Mathis et al. |
| 2005/0113811 A1 | 5/2005 | Houser et al. | 2006/0184088 A1 | 8/2006 | Van Bibber et al. |
| 2005/0119519 A9 | 6/2005 | Girard et al. | 2006/0184203 A1 | 8/2006 | Martin et al. |
| 2005/0131533 A1 | 6/2005 | Alfier et al. | 2006/0184241 A1 | 8/2006 | Marquez |
| 2005/0137449 A1 | 6/2005 | Nieminen et al. | 2006/0190030 A1 | 8/2006 | To et al. |
| 2005/0137450 A1 | 6/2005 | Aronson et al. | 2006/0195012 A1 | 8/2006 | Mortier et al. |
| 2005/0137451 A1 | 6/2005 | Gordon et al. | 2006/0212114 A1 | 9/2006 | Menicanti et al. |
| 2005/0137685 A1 | 6/2005 | Nieminen et al. | 2006/0229717 A1 | 10/2006 | Cohn et al. |
| 2005/0137700 A1 | 6/2005 | Spence et al. | 2006/0235265 A1 | 10/2006 | Alferness et al. |
| 2005/0143811 A1 | 6/2005 | Realyvasquez | 2006/0241340 A1 | 10/2006 | Schroeder et al. |
| 2005/0149179 A1 | 7/2005 | Mathis et al. | 2006/0241656 A1 | 10/2006 | Starksen et al. |
| 2005/0149180 A1 | 7/2005 | Mathis et al. | 2006/0247492 A1 | 11/2006 | Streeter |
| 2005/0149182 A1 | 7/2005 | Alferness et al. | 2006/0252984 A1 | 11/2006 | Rahdert et al. |
| 2005/0159810 A1 | 7/2005 | Filsoufi | 2006/0258900 A1 | 11/2006 | Buckberg et al. |
| 2005/0177228 A1 | 8/2005 | Solem et al. | 2006/0287657 A1 | 12/2006 | Bachman |
| 2005/0184122 A1 | 8/2005 | Hlavka et al. | 2007/0004962 A1 | 1/2007 | Alferness et al. |
| 2005/0187619 A1 | 8/2005 | Mathis et al. | 2007/0038293 A1 | 2/2007 | St. Goar et al. |
| 2005/0192474 A1 | 9/2005 | Vanden Hoek et al. | 2007/0050020 A1 | 3/2007 | Spence |
| 2005/0192666 A1 | 9/2005 | McCarthy | 2007/0055303 A1 | 3/2007 | Vidlund et al. |
| 2005/0197527 A1 | 9/2005 | Bolling | 2007/0066879 A1 | 3/2007 | Mathis et al. |
| 2005/0197528 A1 | 9/2005 | Vanden Hoek et al. | 2007/0100442 A1 | 5/2007 | Solem et al. |
| 2005/0197692 A1 | 9/2005 | Pai et al. | 2007/0112244 A1 | 5/2007 | McCarthy et al. |
| 2005/0197693 A1 | 9/2005 | Pai et al. | 2007/0118155 A1 | 5/2007 | Goldfarb et al. |
| 2005/0209690 A1 | 9/2005 | Mathis et al. | 2007/0123978 A1 | 5/2007 | Cox |
| 2005/0216039 A1 | 9/2005 | Lederman | 2007/0129598 A1 | 6/2007 | Raman et al. |
| 2005/0216077 A1 | 9/2005 | Mathis et al. | 2007/0129737 A1 | 6/2007 | Goldfarb et al. |
| 2005/0216078 A1 | 9/2005 | Starksen et al. | 2007/0156235 A1 | 7/2007 | Rourke et al. |
| 2005/0222488 A1 | 10/2005 | Chang et al. | 2007/0161846 A1 | 7/2007 | Nikolic et al. |

| | | | |
|---|---|---|---|
| 2007/0208211 A1 | 9/2007 | Shapland et al. | |
| 2007/0213814 A1 | 9/2007 | Liddicoat et al. | |
| 2007/0225547 A1 | 9/2007 | Alferness | |
| 2007/0288090 A1 | 12/2007 | Solem et al. | |
| 2008/0033235 A1 | 2/2008 | Shapland et al. | |
| 2008/0051807 A1 | 2/2008 | St. Goar et al. | |
| 2008/0065047 A1 | 3/2008 | Sabbah et al. | |
| 2008/0091191 A1 | 4/2008 | Witzel et al. | |
| 2008/0091264 A1 | 4/2008 | Machold et al. | |
| 2008/0097489 A1 | 4/2008 | Goldfarb et al. | |
| 2008/0097593 A1 | 4/2008 | Bolling et al. | |
| 2008/0097594 A1 | 4/2008 | Mathis et al. | |
| 2008/0109059 A1 | 5/2008 | Gordon et al. | |
| 2008/0109076 A1 | 5/2008 | Cartledge et al. | |
| 2008/0125622 A1 | 5/2008 | Walsh et al. | |
| 2008/0140190 A1 | 6/2008 | Macoviak et al. | |
| 2008/0140191 A1 | 6/2008 | Mathis et al. | |
| 2008/0147184 A1 | 6/2008 | Lattouf | |
| 2008/0154359 A1 | 6/2008 | Salgo et al. | |
| 2008/0161638 A1 | 7/2008 | Taylor et al. | |
| 2008/0167714 A1 | 7/2008 | St. Goar et al. | |
| 2008/0177382 A1 | 7/2008 | Hyde et al. | |
| 2008/0183194 A1 | 7/2008 | Goldfarb et al. | |
| 2008/0183284 A1 | 7/2008 | Ryan et al. | |
| 2008/0188861 A1 | 8/2008 | Ryan et al. | |
| 2008/0195200 A1 | 8/2008 | Vidlund et al. | |
| 2008/0208331 A1 | 8/2008 | McCarthy et al. | |
| 2008/0215008 A1 | 9/2008 | Nance et al. | |
| 2008/0215074 A1 | 9/2008 | Raman et al. | |

FOREIGN PATENT DOCUMENTS

| | | |
|---|---|---|
| DE | 36 14 292 C1 | 11/1987 |
| DE | 42 34 127 A1 | 5/1994 |
| DE | 295 00 381 | 7/1995 |
| DE | 296 19 294 U1 | 8/1997 |
| DE | 298 24 017 U1 | 6/1998 |
| DE | 198 26 675 A1 | 3/1999 |
| DE | 199 47 885 A1 | 4/2000 |
| EP | 0 583 012 A1 | 2/1994 |
| EP | 0 792 621 A1 | 9/1997 |
| EP | 0 820 729 A1 | 1/1998 |
| EP | 1 129 736 A1 | 9/2001 |
| GB | 2 214 428 A | 9/1989 |
| NL | 9 200 878 | 12/1993 |
| WO | WO 91/19465 A1 | 12/1991 |
| WO | WO 95/06447 A1 | 3/1995 |
| WO | WO 95/16407 A1 | 6/1995 |
| WO | WO 95/16476 A1 | 6/1995 |
| WO | WO 98/58598 A1 | 6/1995 |
| WO | WO 96/02197 A1 | 2/1996 |
| WO | WO 96/04852 A1 | 2/1996 |
| WO | WO 96/40356 A1 | 12/1996 |
| WO | WO 97/14286 A2 | 4/1997 |
| WO | WO 97/24082 A1 | 7/1997 |
| WO | WO 97/24083 A1 | 7/1997 |
| WO | WO 97/24101 A1 | 7/1997 |
| WO | WO 97/41779 | 11/1997 |
| WO | WO 98/03213 A1 | 1/1998 |
| WO | WO 98/14136 A1 | 4/1998 |
| WO | WO 98/17347 A1 | 4/1998 |
| WO | WO 98/18393 A1 | 5/1998 |
| WO | WO 98/26738 A1 | 6/1998 |
| WO | WO 98/29041 A1 | 7/1998 |
| WO | WO 98/32382 A1 | 7/1998 |
| WO | WO 98/44969 A1 | 10/1998 |
| WO | WO 99/00059 A1 | 1/1999 |
| WO | WO 99/11201 A2 | 3/1999 |
| WO | WO 99/13777 A1 | 3/1999 |
| WO | WO 99/13936 | 3/1999 |
| WO | WO 99/16350 A1 | 4/1999 |
| WO | WO 99/22784 A1 | 5/1999 |
| WO | WO 99/30647 A1 | 6/1999 |
| WO | WO 99/44534 A1 | 9/1999 |
| WO | WO 99/44680 A1 | 9/1999 |
| WO | WO 99/52470 A1 | 10/1999 |
| WO | WO 99/53977 A1 | 10/1999 |
| WO | WO 99/56655 A1 | 11/1999 |
| WO | WO 99/66969 A1 | 12/1999 |
| WO | WO 00/02500 A1 | 1/2000 |
| WO | WO 00/03759 A2 | 1/2000 |
| WO | WO 00/06026 A2 | 1/2000 |
| WO | WO 00/06028 A1 | 2/2000 |
| WO | WO 00/13722 A1 | 3/2000 |
| WO | WO 00/18320 A1 | 4/2000 |
| WO | WO 00/25842 A1 | 5/2000 |
| WO | WO 00/25853 A2 | 5/2000 |
| WO | WO 00/27304 A1 | 5/2000 |
| WO | WO 00/28912 A1 | 5/2000 |
| WO | WO 00/28918 A1 | 5/2000 |
| WO | WO 00/36995 A2 | 6/2000 |
| WO | WO 00/42919 A1 | 7/2000 |
| WO | WO 00/42950 A2 | 7/2000 |
| WO | WO 00/42951 A1 | 7/2000 |
| WO | WO 00/45735 A1 | 8/2000 |
| WO | WO 00/60995 A2 | 10/2000 |
| WO | WO 00/61033 A1 | 10/2000 |
| WO | WO 00/62715 A1 | 10/2000 |
| WO | WO 00/62727 A1 | 10/2000 |
| WO | WO 01/00111 A1 | 1/2001 |
| WO | WO 01/03608 A1 | 1/2001 |
| WO | WO 01/19291 A1 | 3/2001 |
| WO | WO 01/19292 A1 | 3/2001 |
| WO | WO 01/21070 A1 | 3/2001 |
| WO | WO 01/21247 A1 | 3/2001 |
| WO | WO 01/54562 A2 | 3/2001 |
| WO | WO 01/95832 A1 | 3/2001 |
| WO | WO 01/26557 A1 | 4/2001 |
| WO | WO 01/28432 A1 | 4/2001 |
| WO | WO 01/49217 A2 | 7/2001 |
| WO | WO 01/50981 A1 | 7/2001 |
| WO | WO 01/54618 A1 | 8/2001 |
| WO | WO 01/54745 A2 | 8/2001 |
| WO | WO 01/67985 A1 | 9/2001 |
| WO | WO 01/70116 A1 | 9/2001 |
| WO | WO 01/78625 A1 | 10/2001 |
| WO | WO 01/85061 A2 | 11/2001 |
| WO | WO 01/91667 A2 | 12/2001 |
| WO | WO 01/95830 A2 | 12/2001 |
| WO | WO 01/95831 A2 | 12/2001 |
| WO | WO 02/11625 A2 | 2/2002 |
| WO | WO 02/13726 A2 | 2/2002 |
| WO | WO 02/19917 A1 | 3/2002 |
| WO | WO 02/28450 A2 | 4/2002 |
| WO | WO 02/30292 A1 | 4/2002 |
| WO | WO 02/30335 A2 | 4/2002 |
| WO | WO 02/34167 A2 | 5/2002 |
| WO | WO 02/38081 A2 | 5/2002 |
| WO | WO 02/43617 A2 | 6/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/064035 A1 | 8/2002 |
| WO | WO 02/076284 A2 | 10/2002 |
| WO | WO 02/078576 A2 | 10/2002 |
| WO | WO 02/085251 A1 | 10/2002 |
| WO | WO 02/096275 A2 | 12/2002 |
| WO | WO 03/001893 A2 | 1/2003 |
| WO | WO 03/007778 A2 | 1/2003 |
| WO | WO 03/015611 A2 | 2/2003 |
| WO | WO 03/022131 A2 | 3/2003 |

WO  WO 03/059209 A2  7/2003

OTHER PUBLICATIONS

McGoon, M.D. et al., "Correction of the univentricular heart having two atrioventricular valves," *The Journal of Thoracic and Cardiovascular Surgery*, vol. 74, No. 2, Aug. 1977, pp. 218-226.
Lev, M.D., et al., "Single (Primitive) Ventricle," *Circulation*, vol. 39, May 1969, pp. 577-591.
Westaby with Bosher, "Landmarks in Cardiac Surgery," 1997, pp. 198-199.
Shumacker, "Cardiac Aneurysms," *The Evolution of Cardiac Surgery*, 1992, pp. 159-165.
Feldt, M.D., "Current status of the septation procedure for univentricular heart," *The Journal of Thoracic and Cardiovascular Surgery*, vol. 82, No. 1, Jul. 1981, pp. 93-97.
Doty, M.D., "Septation of the univentricular heart," *The Journal of Thoracic and Cardiovascular Surgery*, vol. 78, No. 3, Sep. 1979, pp. 423-430.
Carpentier et al., "Myocardial Substitution with a Stimulated Skeletal Muscle: First Successful Clinical Case," Letter to the Editor, p. 1267, Sep. 25, 1996.
Ianuzzo et al., "Preservation of the Latissimus Dorsi Muscle During Cardiomyoplasty Surgery "*J. Card. Surg.*, 1996:11:99-108.
Ianuzzo et al., "On Preconditioning of Skeletal Muscle: Application to Dynamic Cardiomyoplasty," Invited Commentary, *J. Card. Surg.*, 1996:11:109-110.
Chachques et al., "Latissimus Dorsi Dynamic Cardiomyoplasty," *Ann. Thorac. Surg.*, 1989:47:600-604.
Moreira et al., "Latissimus Dorsi Cardiomyoplasty in the Treatment of Patients with Dilated Cardiomyopathy," Supplement IV Circulation, Sep. 25, 1996, 7 pgs.
Lucas et al., "Long-Term Follow-Up (12 to 35 Weeks) After Dynamic Cardiomyoplasty," *JACC*, vol. 22, No. 3, Sep. 1993:758-67.
Batista et al., "Partial Left Ventriculectomy to Improve Left Ventricular Function in End-Stage Heart Disease," *J. Card. Surg.*, 1996:11:96-98.
"Congestive Heart Failure in the United States: A New Epidemic" Data Fact Sheet, National Heart, Lung, and Blood Institute, National Institutes of Health, Dec. 9, 1996, pp. 1-6.
Kormos et al., "Experience with Univentricular Support in Mortally III Cardiac Transplant Candidates " *Ann. Thorac. Surg.*, 1990:49:261-71.
Wampler et al., "Treatment of Cardiogenic Shock with the Hemopump Left Ventricular Assist Device," *Ann. Thorac. Surg.*, 1991:52:506-13.
McCarthy et al., "Clinical Experience with the Novacor Ventricular Assist System," *J. Thorac. Cardiovasc. Surg.*, 1991:102-578-87.
Burnett et al., "Improved Survival After Hemopump Insertion in Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.
Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.
Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.
Bearnson et al., "Development of a Prototype Magnetically Suspended Rotor Ventricular Assist Device," *ASAIO Journal*, 1996, pp. 275-280.
Sakakibara et al., "A Muscle Powered Cardiac Assist Device for Right Ventricular Support: Total Assist or Partial Assist?," *Trans. Am.Soc. Artif. Intern. Organs*, Vol. XXXVI, 1990, pp. 372-375.
Medtronic, Inc. 1996 Annual Shareholders Report, 79 pages.
ABIOMED, Inc. Annual Report 1996, 32 pages.
Press Release dated Sep. 16, 1996, "ABIOMED Wins $8.5 Million Federal Contract to Qualify its Artificial Heart for Human Trials," 5 pages.
Press Release dated Sep. 26, 1996, ABIOMED's Temporary Artificial Heart System Reaches 200 U.S. Medical Center Milestone, 1 page.
Press Release dated May 17, 1996, "ABIOMED Receives FDA Approval to Expand Indications for Use of Cardiac Assist System," 1 page.
Press Release dated Oct. 3, 1995, "ABIOMED Wins $4.35 Million Contract from the National Heart, Lung and Blood Institutes to Develop Implantable Heart Booster," 1 page.
Press Release dated Sep. 29, 1995, "ABIOMED" Wins NIH Grant to Develop Calcification-Resistant Plastic Heart Valve, 1 page.
Press Release dated Aug. 25, 1995, "ABIOMED Wins Research Grant from NIH to Develop Suturing Instrument for Abdominal surgery," 1 page.
Press Release dated Aug. 11, 1995, "ABIOMED Receives Grant from NIH to Develop Disposable Bearingless Centrifugal Blood Pump," 1 page.
Press Release dated Jun. 9, 1995, "ABIOMED Receives Grant from National Institutes of Health to Develop a Laser Welding Technique for Tissue Repair," 1 page.
Press Release dated Apr. 27, 1995, "ABIOMED's Temporary Artificial Heart System Reaches 1,000 Patient Milestone; BVS-5000 in More Than 100 U.S. Medical Centers," 1 page.
"Reversible Cardiomyopathy," *Thoratec's Heartbeat*, vol. 10.2, Aug. 1996, 4 pages.
Tsai et al., "Surface Modifying Additives for Improved Device-Blood Compatibility," *ASAIO Journal*, 1994, pp. 619-624.
Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349.
Brochure entitled "Thoratec Ventricular Assist Device System—Because Heart Patients Come in All Sizes," date even with or prior to Jan. 2, 1997, 5 pages.
Press Release dated Oct. 3, 1994, "Heartmate System Becomes First Implantable Cardiac-Assist Device to be Approved for Commercial Sale in the U.S.," 2 pages.
Bocchi et al., "Clinical Outcome after Surgical Remodeling of Left Ventricle in Candidates to Heart Transplantation with Idiopathic Dilated Cardiomypathy—Short Term Results," date even with or prior to Jan. 2, 1997, 1 page.
Bach et al., "Early Improvement in Congestive Heart Failure after Correction of Secondary Mitral Regurgitation in End-Stage Cardiomyopathy," *American Heart Journal*, Jun. 1995, pp. 1165-1170.
Schuler et al., "Temporal Response of Left Ventricular Performance to Mitral Valve Surgery," vol. 59, No. 6, Jun. 1979, pp. 1218-1231.
Huikuri, "Effect of Mitral Valve Replacement on Left Ventricular Function in Mitral Regurgitation," *Br. Heart J.*, vol. 49, 1983, pp. 328-333.
Pitarys II et al., "Long-Term Effects of Excision of the Mitral Apparatus on Global and Regional Ventricular Function in Humans," *JACC*, vol. 15, No. 3, Mar. 1, 1990, pp. 557-563.
Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.
Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.
Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.
McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.
Alonso-Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404-406, Oct. 1987.

Savage, M.D., "Repair of left ventricular aneurysm," *The Journal of Thoracic and Cardiovascular Surgery*, vol. 104, No. 3, Sep. 1992, pp. 752-762.

Melvin, "Ventricular Radius Reduction Without Resection: A Computational Analysis," *ASAIO Journal*, 45:160-165, 1999.

Cox, "Left Ventricular Aneurysms: Pathophysiologic Observations and Standard Resection " *Seminars in Thoracic and Cardiovascular Surgery*, vol. 9, No. 2, Apr. 1997, pp. 113-122.

Boyd et al., "Tricuspid Annuloplasty," *The Journal of Thoracic Cardiovascular Surgery*, vol. 68, No. 3, Sep. 1974, 8 pages.

Melvin, "Reduction of Ventricular Wall Tensile Stress by Geometric Remodeling Device", 1 page, undated.

Kay et al., "Surgical Treatment of Mitral Insufficiency", *The Journal of Thoracic Surgery*, 1955, 29:618-620.

Harken et al., "The Surgical Correction of Mitral Insufficiency", *The Journal of Thoracic Surgery*, 1954, 28:604-627.

Bailey et al., "Closed Intracardiac Tactile Surgery", *Diseases of the Chest*, 1952, XXII:1-24.

Sakakibara, "A Surgical Approach to the Correction of Mitral Insufficiency", *Annals of Surgery*, 1955, 142:196-203.

Glenn et al., "The Surgical Treatment of Mitral Insufficiency: The Fate of A Vascularized Transchamber Intracardiac Graft", *Annals of Surgery*, 1955, 141:4:510-518.

Kay et al., "Surgical Treatment of Mitral Insufficiency", *Surgery*, 1955, 37:5:697-706.

Bailey et al., "The Surgical Correction of Mitral Insufficiency By The Use of Pericardial Grafts" *The Journal of Thoracic Surgery*, 1954, 28:6:551-603.

Harken et al., "The Surgical Correction of Mitral Insufficency", *Surgical Forum* 1953, 4:4-7.

Shumacker, Jr., "Attempts to Control Mitral Regurgitation", *The Evolution of Cardiac Surgery*, 1992, 203-210.

acorn cardiovascular, inc., "Acorn Cardiovascular Summary", undated.

acorn cardiovascular, inc., "Acorn Cardiovascular Company Overview", undated.

Batista, MD et al., "Partial Left Ventriculectomy to Treat End-Stage Heart Disease", *Ann. Thorac. Surg.*, 64:634-8, 1997.

Melvin DB et al., Reduction of Ventricular Wall Tensile Stress by Geometric Remodeling Device, *Poster text, ASAIO* 1999.

Hayden et al., "Scintiphotographic Studies of Acquired Cardiovascular Disease," *Seminars in Nuclear Medicine*, vol. III, No. 2, Apr. 1973, pp. 177-190.

McCarthy, Transcription of Mar. 13, 2000 presentation given at ACC.

acorn cardiovascular, inc., "Acorn Cardiovascular Abstracts", Nov. 13, 2000.

Nation's First "Heart Jacket" Surgery to Treat Heart Failure Performed at HUP: Novel "Cardiac Support Device" Comes to America After Promising Results in Europe, Jun. 26, 2000.

acorn cardiovascular, inc., Acorn Cardiovascular Company Overview, undated, 1 page.

acorn cardiovascular, inc., Acorn Cardiovascular Company Overview, Jun. 2000.

acorn cardiovascular, inc., Acorn Cardiovascular Business Plan, May 2000.

acorn cardiovascular, inc., "Acorn Cardiovascular Highlights Abstracts", Mar. 10, 1999.

acorn cardiovascular, inc., "Acorn Cardiovascular Highlights Abstracts", Apr. 19, 1999.

acorn cardiovascular, inc., "Acorn Cardiovascular Highlights Abstracts", Oct. 1, 1999.

acorn cardiovascular, inc., "Acorn Cardiovascular Highlights Abstracts", Nov. 9, 1999.

Melvin DB, "Ventricular Radius-Reduction Without Resection A Computational Assessment", undated.

Timek, Thomasz A., MD, et al, The Journal of Thoracic Surgery, vol. 123, No. 5 Surgery for Acquired Cardiovascular Disease, *Septal-lateral annular cinching abolishes acute ischemic mitral regurgitation*.

Timek, Thomasz A. et al, Department of Cardiothoracic Surgery and Division of Cardiovascular Medicine, Stanford University School of Medicine, Stanford, CA, *Septal-Lateral Annular Cinching ('SLAC') reduces Mitral Annular Size without Perturbing Normal Annular Dynamics*, 2002.

Hung, Judy MD et al., *Reverse Ventricular Remodeling Reduces Ischemic Mitral Regurgitation: Echo-Guided Device Application in the Beating Hear*, Circulation, www.circulationaha.org, Nov. 12, 2002.

Bairn, Donald S., MD, Brigham and Women's Hospital, Harvard Medical School, *Percutaneous Treatment of Mitral Regurgitation*, 2005.

Dullum, Mercedes K.C., *Update on Restraint Devices for Congestive Heart Failure*, Abstract and copy of presentation slides given at Tech-Con 2005 for Society of Thoracic Surgeons, Jan. 23, 2005, 11 pages.

"Heart 'jacket' could help stop heart failure progress," *Clinica*, Jul. 10, 2000.

McCarthy et al., "Device Based Left Ventricular Shape Change Immediately Reduces Left Ventricular Volume and Increases Ejection Fraction in a Pacing Induced Cardiomyopathy Model in Dogs: A Pilot Study," JACC, Feb. 2000.

Alonso-Lej, *The Journal of Thoracic and Cardiovascular Surgery*, vol. 68, No. 3, Sep. 1974, p. 349.

European Search Report for corresponding EP Application No. 07109612 dated Nov. 2, 2007.

Hayden et al., "Scintiphotographic Studies of Acquired Cardiovascular Disease," *Seminars in Nuclear Medicine*, vol. III, No. 2, Apr. 1973, pp. 177-190.

\* cited by examiner

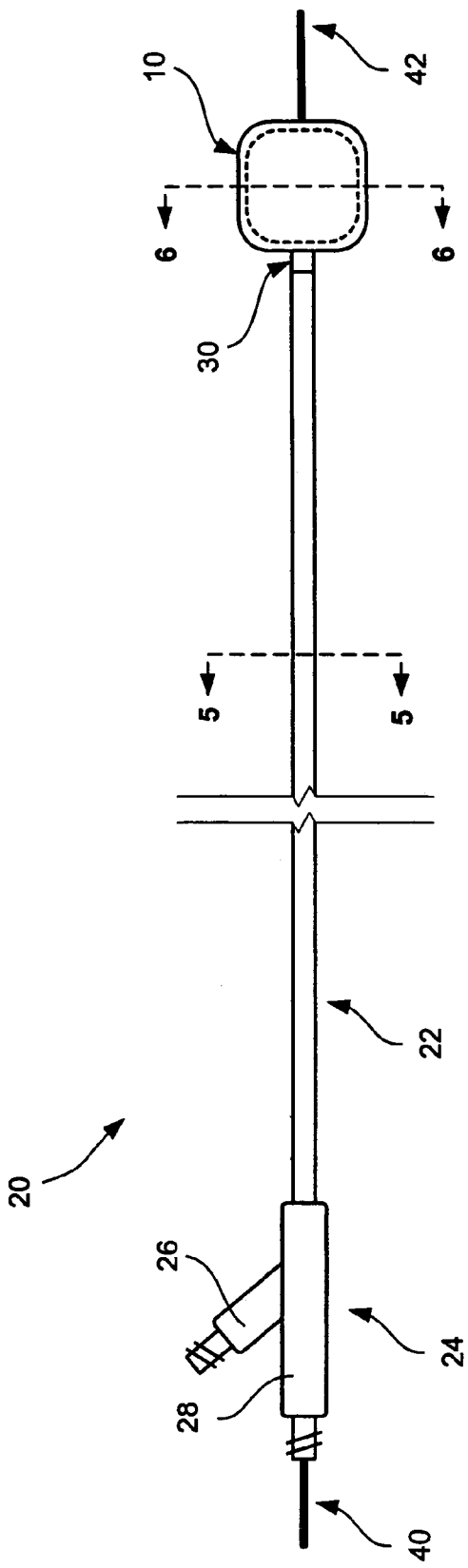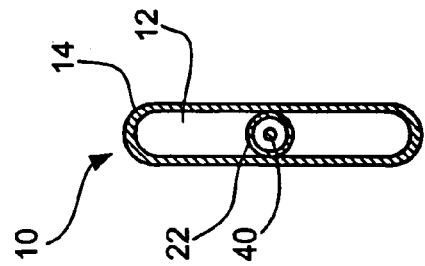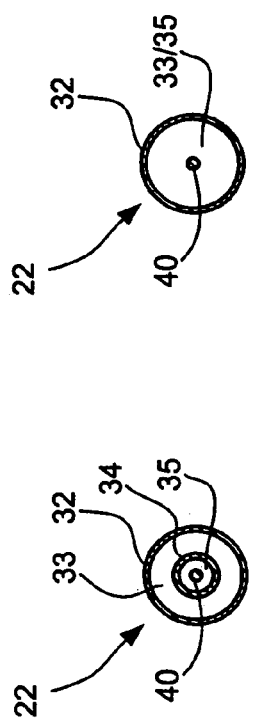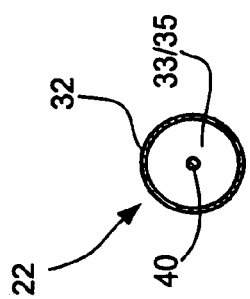
FIG. 4
FIG. 5A
FIG. 5B
FIG. 6

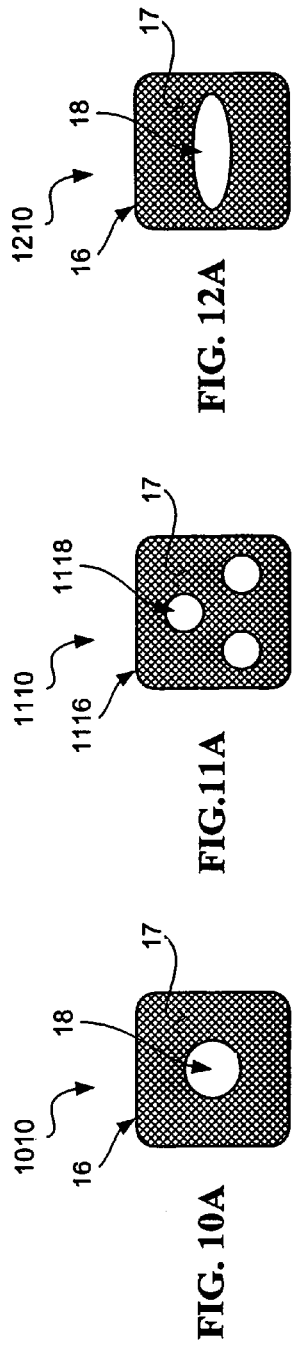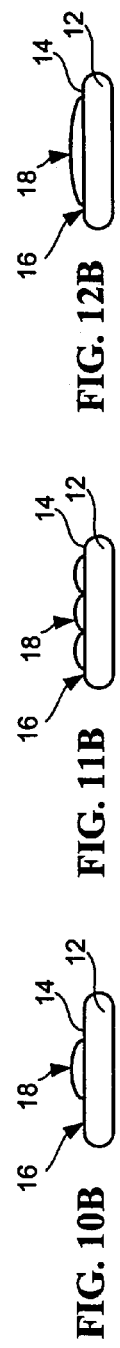

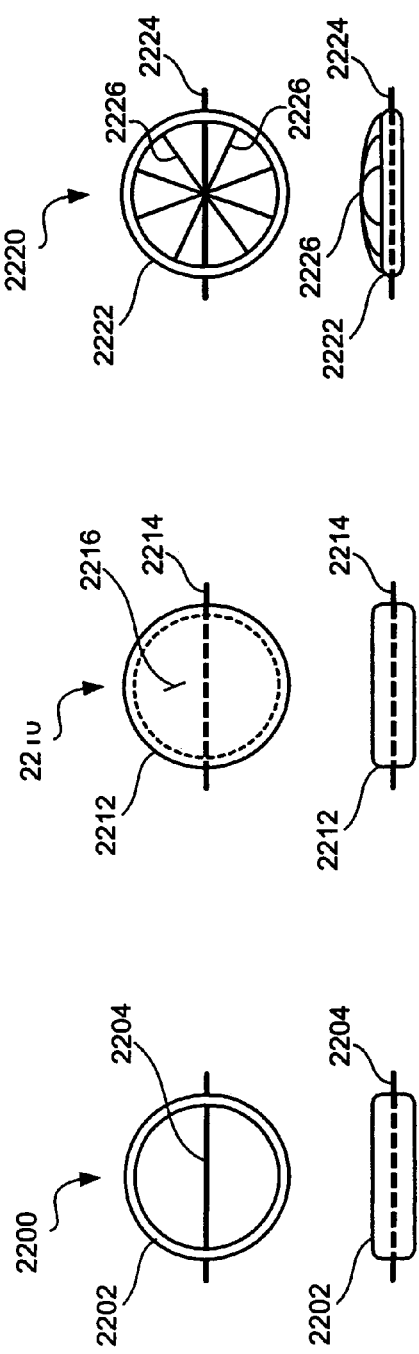

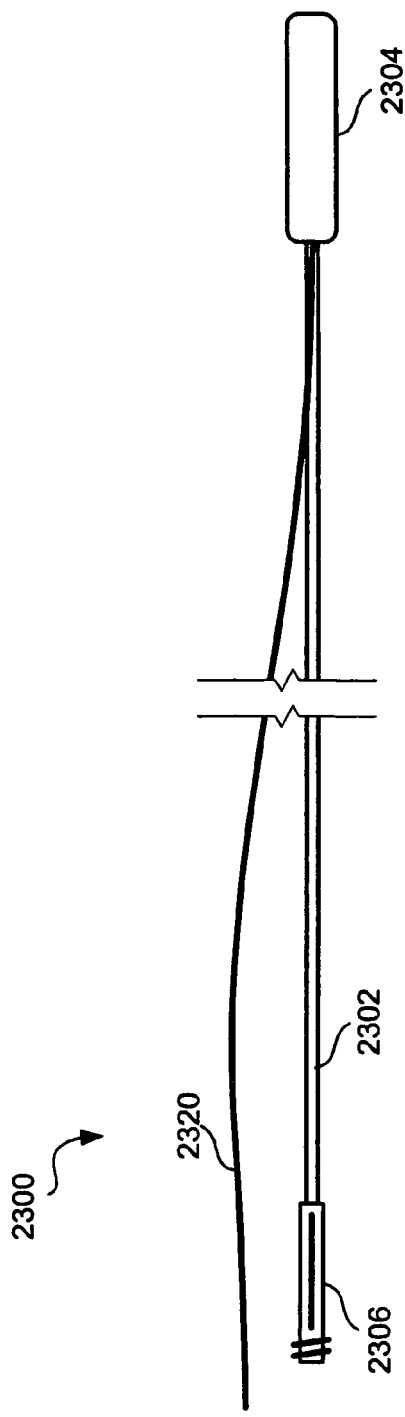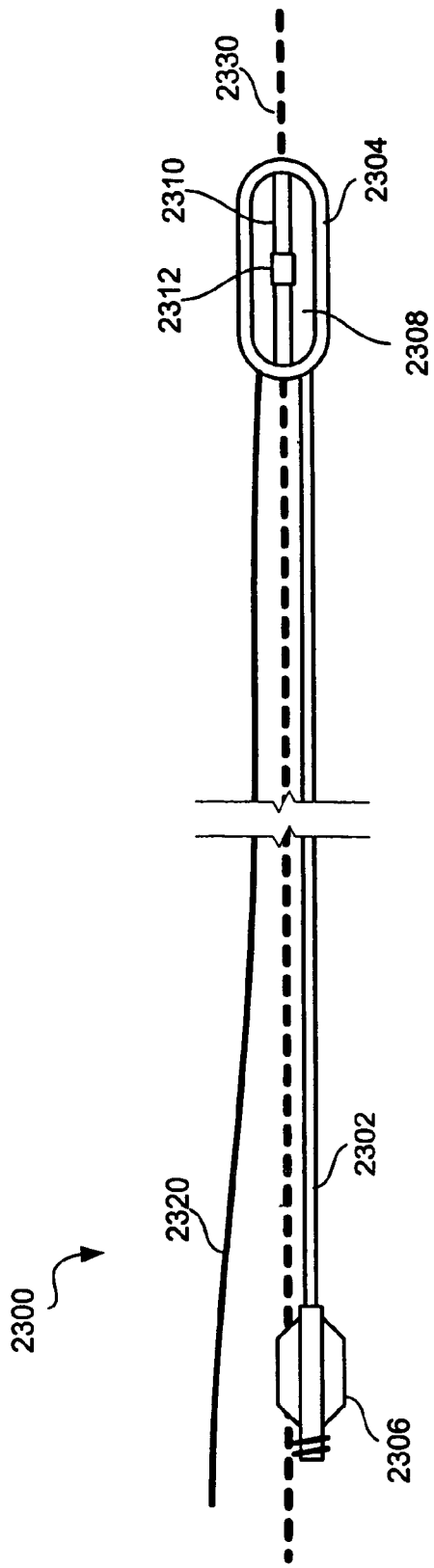
FIG. 23A
FIG. 23B

DEVICES AND METHODS FOR HEART VALVE TREATMENT

CROSS-REFERENCE TO RELATED APPLICATIONS

This application claims the benefits of priority of U.S. Provisional Application No. 60/425,519, filed Nov. 12, 2002, the entire contents of which are incorporated by reference herein.

This application is a continuation of application Ser. No. 10/704,143, filed Nov. 10, 2003, now U.S. Pat. No. 7,112,219, the contents of which are relied upon and incorporated herein by reference.

FIELD OF THE INVENTION

The present invention relates to devices and associated methods for treating and improving the performance of dysfunctional heart valves. More particularly, the invention relates to devices and methods that passively assist to reshape a dysfunctional heart valve to improve its performance.

BACKGROUND OF THE INVENTION

Various etiologies may result in heart valve insufficiency depending upon both the particular valve as well as the underlying disease state of the patient. For instance, a congenital defect may be present resulting in poor coaptation of the valve leaflets, such as in the case of a monocusp aortic valve, for example. Valve insufficiency also may result from an infection, such as rheumatic fever, for example, which may cause a degradation of the valve leaflets. Functional regurgitation also may be present. In such cases, the valve components may be normal pathologically, yet may be unable to function properly due to changes in the surrounding environment. Examples of such changes include geometric alterations of one or more heart chambers and/or decreases in myocardial contractility. In any case, the resultant volume overload that exists as a result of an insufficient valve may increase chamber wall stress. Such an increase in stress may eventually result in a dilatory process that further exacerbates valve dysfunction and degrades cardiac efficiency.

Mitral valve regurgitation often may be driven by the functional changes described above. Alterations in the geometric relationship between valvular components may occur for numerous reasons, including events ranging from focal myocardial infarction to global ischemia of the myocardial tissue. Idiopathic dilated cardiomyopathy also may drive the evolution of functional mitral regurgitation. These disease states often lead to dilatation of the left ventricle. Such dilatation may cause papillary muscle displacement and/or dilatation of the valve annulus. As the papillary muscles move away from the valve annulus, the chordae connecting the muscles to the leaflets may become tethered. Such tethering may restrict the leaflets from closing together, either symmetrically or asymmetrically, depending on the relative degree of displacement between the papillary muscles. Moreover, as the annulus dilates in response to chamber enlargement and increased wall stress, increases in annular area and changes in annular shape may increase the degree of valve insufficiency. Annular dilatation is typically concentrated on the posterior aspect, since this aspect is directly associated with the dilating left ventricular free wall and not directly attached to the fibrous skeleton of the heart. Annular dilatation also may result in a flattening of the valve annulus from its normal saddle shape.

Alterations in functional capacity also may cause valve insufficiency. In a normally functioning heart, the mitral valve annulus contracts during systole to assist in leaflet coaptation. Reductions in annular contractility commonly observed in ischemic or idiopathic cardiomyopathy patients therefore hamper the closure of the valve. Further, in a normal heart, the papillary muscles contract during the heart cycle to assist in maintaining proper valve function. Reductions in or failure of the papillary muscle function also may contribute to valve regurgitation. This may be caused by infarction at or near the papillary muscle, ischemia, or other causes, such as idiopathic dilated cardiomyopathy, for example.

The degree of valve regurgitation may vary, especially in the case of functional insufficiency. In earlier stages of the disease, the valve may be able to compensate for geometric and/or functional changes in a resting state. However, under higher loading resulting from an increase in output requirement, the valve may become incompetent. Such incompetence may only appear during intense exercise, or alternatively may be induced by far less of an exertion, such as walking up a flight of stairs, for example.

Conventional techniques for managing mitral valve dysfunction include either surgical repair or replacement of the valve or medical management of the patient. Medical management typically applies only to early stages of mitral valve dysfunction, during which levels of regurgitation are relatively low. Such medical management tends to focus on volume reductions, such as diuresis, for example, or afterload reducers, such as vasodilators, for example.

Early attempts to surgically treat mitral valve dysfunction focused on replacement technologies. In many of these cases, the importance of preserving the native subvalvular apparatus was not fully appreciated and many patients often acquired ventricular dysfunction or failure following the surgery. Though later experience was more successful, significant limitations to valve replacement still exist. For instance, in the case of mechanical prostheses, lifelong therapy with powerful anticoagulants may be required to mitigate the thromboembolic potential of these devices. In the case of biologically derived devices, in particular those used as mitral valve replacements, the long-term durability may be limited. Mineralization induced valve failure is common within ten years, even in younger patients. Thus, the use of such devices in younger patient groups is impractical.

Another commonly employed repair technique involves the use of annuloplasty rings. These rings originally were used to stabilize a complex valve repair. Now, they are more often used alone to improve mitral valve function. An annuloplasty ring has a diameter that is less than the diameter of the enlarged valve annulus. The ring is placed in the valve annulus and the tissue of the annulus sewn or otherwise secured to the ring. This causes a reduction in the annular circumference and an increase in the leaflet coaptation area. Such rings, however, generally flatten the natural saddle shape of the valve and hinder the natural contractility of the valve annulus. This may be true even when the rings have relatively high flexibility.

To further reduce the limitations of the therapies described above, purely surgical techniques for treating valve dysfunction have evolved. Among these surgical techniques is the Alfiere stitch or so-called bowtie repair. In this surgery, a suture is placed substantially centrally across the valve orifice joining the posterior and anterior leaflets to create leaflet apposition. Another surgical technique includes plication of the posterior annular space to reduce the cross-sectional area of the valve annulus. A limitation of each of these techniques is that they typically require opening the heart to gain direct access to the valve and the valve annulus. This generally necessitates the use of cardiopulmonary bypass, which may introduce additional morbidity and mortality to the surgical procedures. Additionally, for each of these procedures, it is very difficult to evaluate the efficacy of the repair prior to the conclusion of the operation.

Due to these drawbacks, devising effective techniques that could improve valve function without the need for cardiopulmonary bypass and without requiring major remodeling of the valve may be advantageous. In particular, passive techniques to change the shape of the heart chamber and/or associated valve and reduce regurgitation while maintaining substantially normal leaflet motion may be desirable. Further, advantages may be obtained by a technique that reduces the overall time a patient is in surgery and under the influence of anesthesia. It also may be desirable to provide a technique for treating valve insufficiency that reduces the risk of bleeding associated with anticoagulation requirements of cardiopulmonary bypass. In addition, a technique that can be employed on a beating heart would allow the practitioner an opportunity to assess the efficacy of the treatment and potentially address any inadequacies without the need for additional bypass support.

SUMMARY OF THE INVENTION

To address these needs, the present invention provides, in exemplary non-limiting embodiments, devices and methods for improving the function of a valve (e.g., mitral valve) by positioning a spacing filling device outside and adjacent the heart wall such that the device applies an inward force against the heart wall acting on the valve. The device may be remotely secured to the heart wall. The securement may provide a substantially equal and opposite force to the inward force, or a substantially equal and opposite outward force may be applied against anatomical structure outside the heart wall. The inward force is sufficient to change the function of the valve, and may increase coaptation of the leaflets, for example. The spacing filling device may be implanted outside the epicardium, such as between the epicardium and the pericardium, and may be attached to epicardium while remaining free of the pericardium.

The space filling device may be implanted by a surgical approach, a transthoracic approach, or a transluminal approach, for example. The space filling device may be delivered utilizing a delivery catheter navigated via the selected approach, and the space filling device may be expandable between a smaller delivery configuration and a larger deployed configuration. For example, the space filling device may include an expandable structure such as a balloon or a mechanical structure. The balloon may be filled with a liquid, a curable liquid, a solid, or a semi-solid, for example, and may include a mechanical reinforcement member disposed therein. The expandable balloon may be inflated upon implantation or subsequently by, for example, a transdermally accessible port fluidly connected to the balloon.

BRIEF DESCRIPTION OF THE DRAWINGS

FIG. 4 is a schematic plan view of a catheter and guide wire for use in delivering space filling devices by transluminal techniques;

FIGS. 5A and 5B are cross sectional views of the catheter shown in FIG. 4 taken along line 5-5;

FIG. 6 is a cross sectional view of the catheter shown in FIG. 4 taken along line 6-6;

FIGS. 10-22 are schematic illustrations of various design alternatives of space filling devices; and FIGS. 23A and 23B are schematic views of a catheter for use in delivering space filling devices by transthoracic techniques.

DETAILED DESCRIPTION OF THE INVENTION

Figures 1A, 1B:
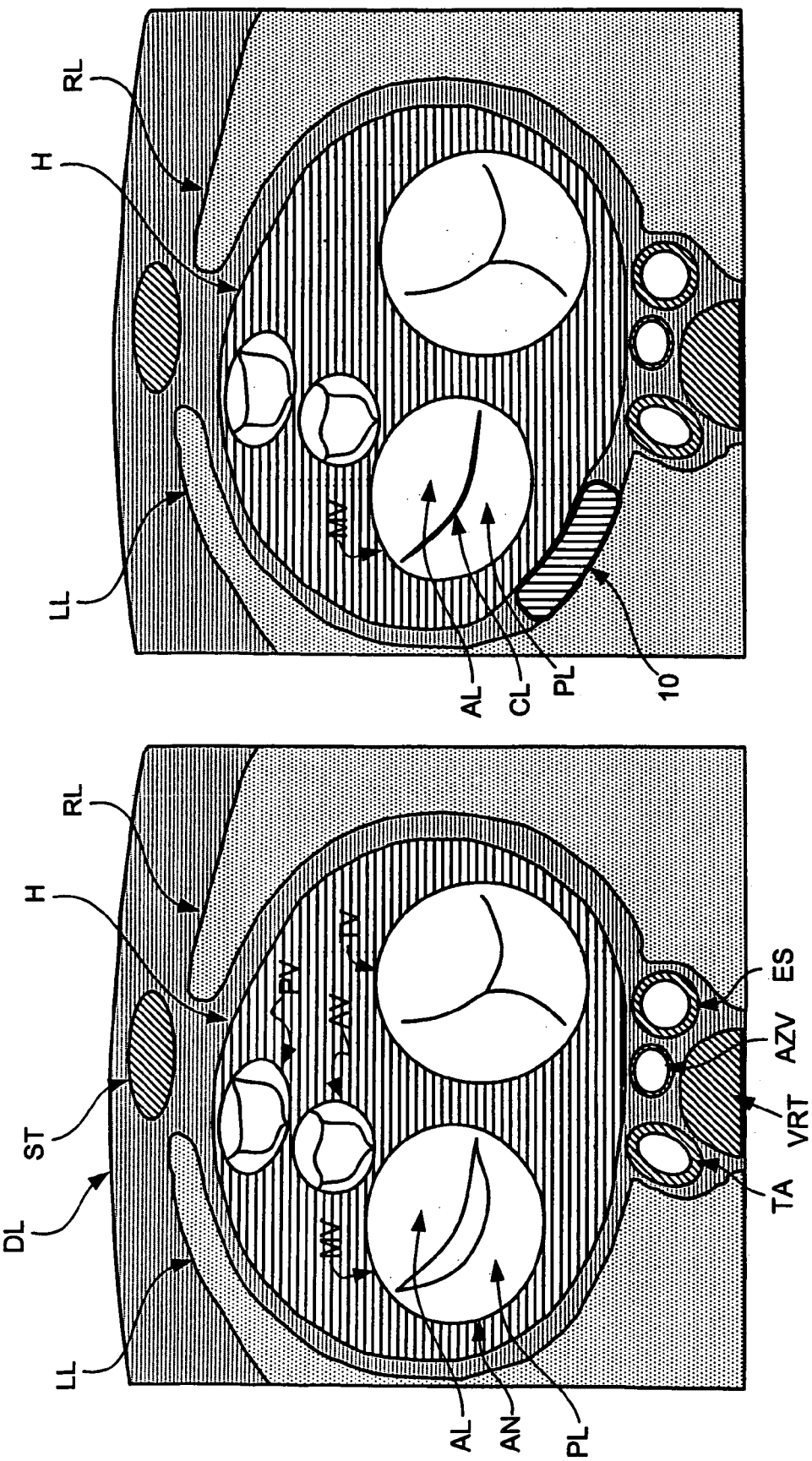
FIGS. 1A-1D are cross sectional views of a patient's trunk at the level of the mitral valve of the heart, showing the effects of space filling devices on mitral valve function.

The following detailed description should be read with reference to the drawings in which similar elements in different drawings are numbered the same. The drawings, which are not necessarily to scale, depict illustrative embodiments and are not intended to limit the scope of the invention.

General Description of Space Filling Device Function and Use

The various aspects of the devices and methods described herein generally pertain to devices and methods for treating heart conditions, including, for example, dilatation, valve incompetencies, including mitral valve leakage, and other similar heart failure conditions. Each disclosed device may operate passively in that, once placed in the heart, it does not require an active stimulus, either mechanical, electrical, hydraulic, pneumatic, or otherwise, to function. Implanting one or more of the devices operates to assist in the apposition of heart valve leaflets to improve valve function.

In addition, these devices may either be placed in conjunction with other devices that, or may themselves function to, alter the shape or geometry of the heart, locally and/or globally, and thereby further increase the heart's efficiency. That is, the heart experiences an increased pumping efficiency through an alteration in its shape or geometry and concomitant reduction in stress on the heart walls, and through an improvement in valve function.

However, the devices disclosed herein for improving valve function can be "stand-alone" devices, that is, they do not necessarily have to be used in conjunction with additional devices for changing the shape of a heart chamber or otherwise reducing heart wall stress. It also is contemplated that a device for improving valve function may be placed relative to the heart without altering the shape of the chamber, and only altering the shape of the valve itself. In other words, the devices and methods described herein involve geometric reshaping of portions of the heart and treating valve incompetencies. In some embodiments of the devices and methods described herein, only a localized portion of the heart is altered to treat valve incompetencies. In other embodiments, the entire chamber geometry may be altered to return the heart to a more normal state of stress.

The devices and methods described herein offer numerous advantages over the existing treatments for various heart conditions, including valve incompetencies. The devices are relatively easy to manufacture and use, and the transluminal, transthoracic, and surgical techniques and tools for implanting the devices do not require the invasive procedures of current surgical techniques. For instance, these techniques do not require removing portions of the heart tissue, nor do they necessarily require opening the heart chamber or stopping the heart during operation. For these reasons, the techniques for implanting the devices disclosed herein also are less risky to the patient than other techniques. The less invasive nature of these techniques and tools may also allow for earlier intervention in patients with heart failure and/or valve incompetencies.

Although the methods and devices are discussed hereinafter in connection with their use for the mitral valve of the heart, these methods and devices may be used for other valves of the heart for similar purposes. One of ordinary skill in the art would understand that the use of the devices and methods described herein also could be employed for other valves of the heart. The mitral valve has been selected for illustrative purposes because a large number of the disorders occur in connection with the mitral valve.

The devices and methods described herein are discussed herein with reference to the human heart H, but may be equally applied to other animal hearts not specifically mentioned herein. For purposes of discussion and illustration, several anatomical features are labeled as follows: left ventricle LV; right ventricle RV; left atrium LA; ventricular septum VS; right ventricular free wall RVFW; left ventricular free wall LVFW; atrioventricular groove AVG; mitral valve MV; tricuspid valve TV; aortic valve AV; pulmonary valve PV; papillary muscle PM; chordae tendeneae CT (or simply chordae); anterior leaflet AL; posterior leaflet PL; coaptation line CL; annulus AN; ascending aorta AA; thoracic aorta TA; pulmonary trunk PT; inferior vena cava IVC; superior vena cava SVC; azygos vein AZV; coronary sinus CS; cardiac vein CV; right coronary artery RCA; left anterior descending artery LAD; circumflex artery CFX; left lung LL; right lung RL; dermal layer DL; sternum ST; xiphoid XPH; diaphragm DPH; vertebrae VRT; esophagus ES; and trachea TR.

With reference to FIG. 1A-1D, cross sectional views of a patient's trunk at the level of the mitral valve MV of the heart H show the effects of a space filling devices 10 on mitral valve MV function. As seen in FIG. 1A, an incompetent mitral valve MV is shown during systole, as rendered incompetent by, for example, a dilated valve annulus AN, a displaced papillary muscle PM due to ventricular dilation or other mechanism. As seen in FIG. 1B, the formerly incompetent mitral valve MV is shown during systole as corrected with space filling device 10. The space filling device 10 causes inward displacement of a specific portion of the heart wall adjacent the mitral valve MV resulting in re-configuration and re-shaping of the annulus AN and/or the papillary muscles PM, thus providing more complete closure of the mitral valve leaflets AL/PL during systole, as shown by closed coaptation line CL in FIG. 1B.

Figure 1D:
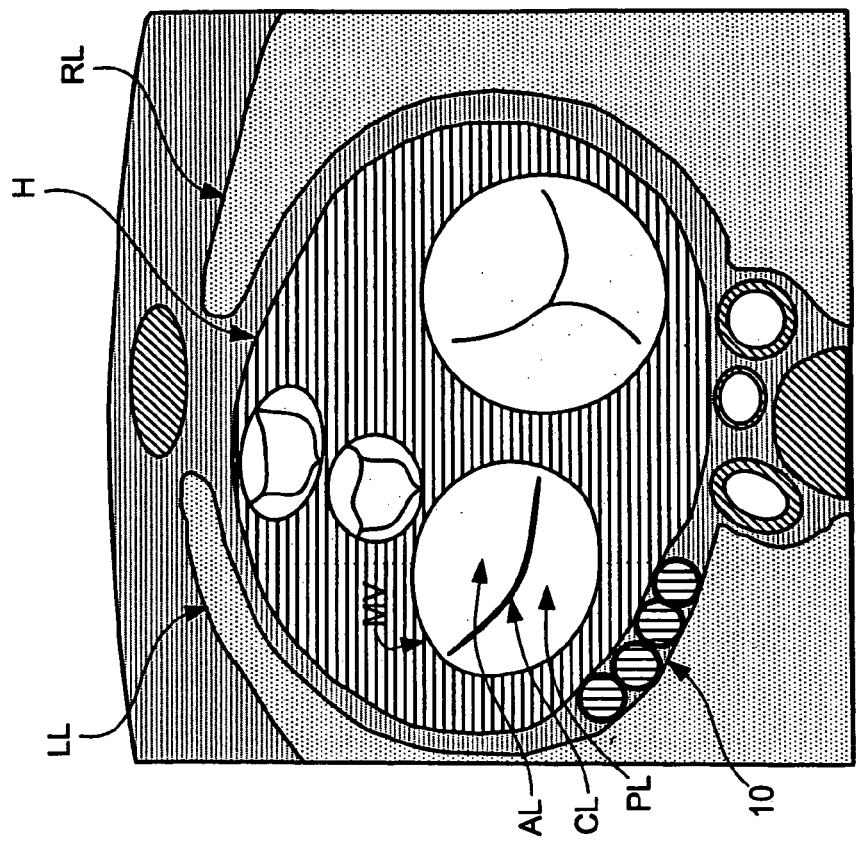
Figure 1C:
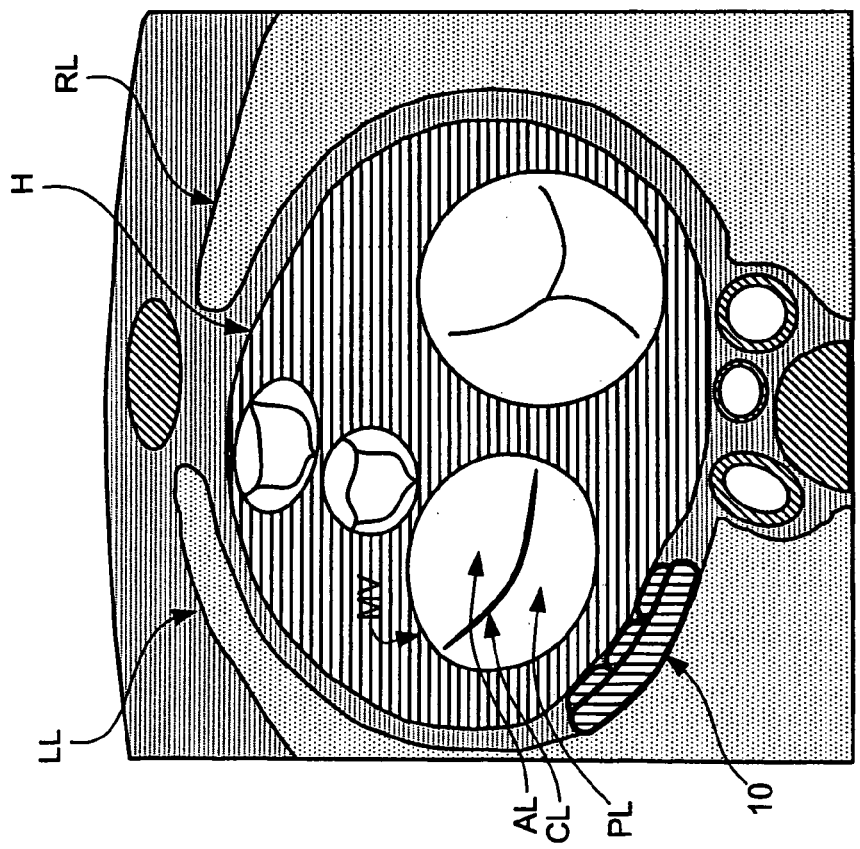

As shown in FIGS. 1B-1D, the space filling device 10 may be positioned outside and adjacent the heart wall such that the device 10 applies an inward force against the heart wall acting on the mitral valve MV. A substantially equal and opposite force may be provided by securing the device 10 to the heart wall, and/or a substantially equal and opposite outward force may be applied against anatomical structure outside the heart wall, such as left lung LL as shown. The inward force may be applied throughout the cardiac cycle. The size of the device 10 is sufficient to push away from anatomical structure outside the heart wall and push against the heart wall and act on the mitral valve MV in order to change the function of the mitral valve MV, such as increasing coaptation of the leaflets PL/AL. To maximize the effectiveness of the inward force, the device may be sized, configured and positioned to create a normal force against the heart wall that is generally orthogonal to the coaptation line CL formed by the leaflets PL/AL. This may be achieved, for example, by positioning the device 10 in a posterior-lateral projection of the mitral valve MV generally orthogonal to the middle tangent of the coaptation line CL.

The space filling device 10 occupies sufficient space outside the epicardium of the heart H to generate the inward force described above. To this end, the space filling device 10 may take on a number of different sizes, shapes and configurations, some of which are described in detail herein with reference to FIGS. 10-17. For example, as seen in FIG. 1B, the space filling device comprises a generally uniform mass or protrusion. Alternatively, the space filling device 10 may comprise a plurality of integral protrusions as seen in FIG. 1C or a plurality of individual protrusions as seen in FIG. 1D.

Figures 2A, 2B:
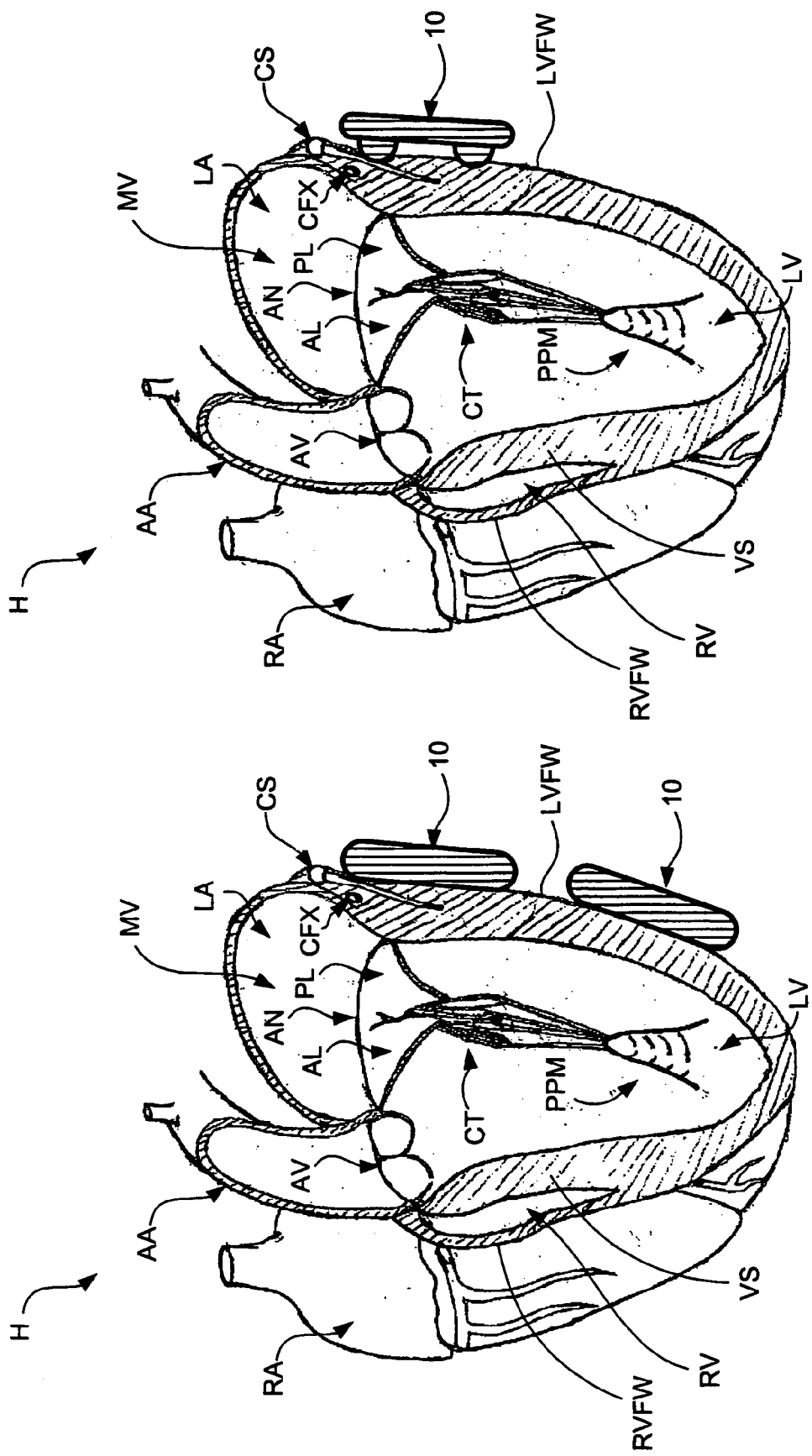
FIGS. 2A-2B are long axis cross sectional views of a patient's heart showing space filling devices in various positions.

The space filling device 10 may also take on a number of different implanted positions, a select few of which are described herein for purposes of illustration, not necessarily limitation. In the short axis view as seen in FIGS. 1B-1D, the space filling device 10 may extend along all of, a portion of, or beyond the posterior-lateral projection of the mitral valve MV. In the long axis view as seen in FIGS. 2A and 2B, the space filling device 10 may extend along all of, a portion of, or beyond the posterior-lateral projection of the mitral valve MV structures, including the papillary muscles PM, the chordae CT, the leaflets PL/AL, and the annulus AN. For example, as seen in FIG. 2A, the space filling device 10 may be positioned adjacent the annulus AN (e.g., extending slightly above and below the annulus AN near the AV groove), or adjacent the papillary muscles PM (e.g., extending slightly above and below the papillary muscles PM). To avoid compression of the coronary arteries and cardiac veins, the space filling device 10 may have a relatively large surface area in contact with the heart wall as shown in FIG. 2A, or the space filling device 10 may have relatively small contact areas selected and positioned to establish contact with the heart wall while avoiding compression of the coronary arteries and cardiac veins as shown in FIG. 2B. For example, the space filling device 10 may be positioned inferior of the circumflex artery between the second and third obtuse marginals.

Description of Delivery Techniques and Approaches

Figure 3A:
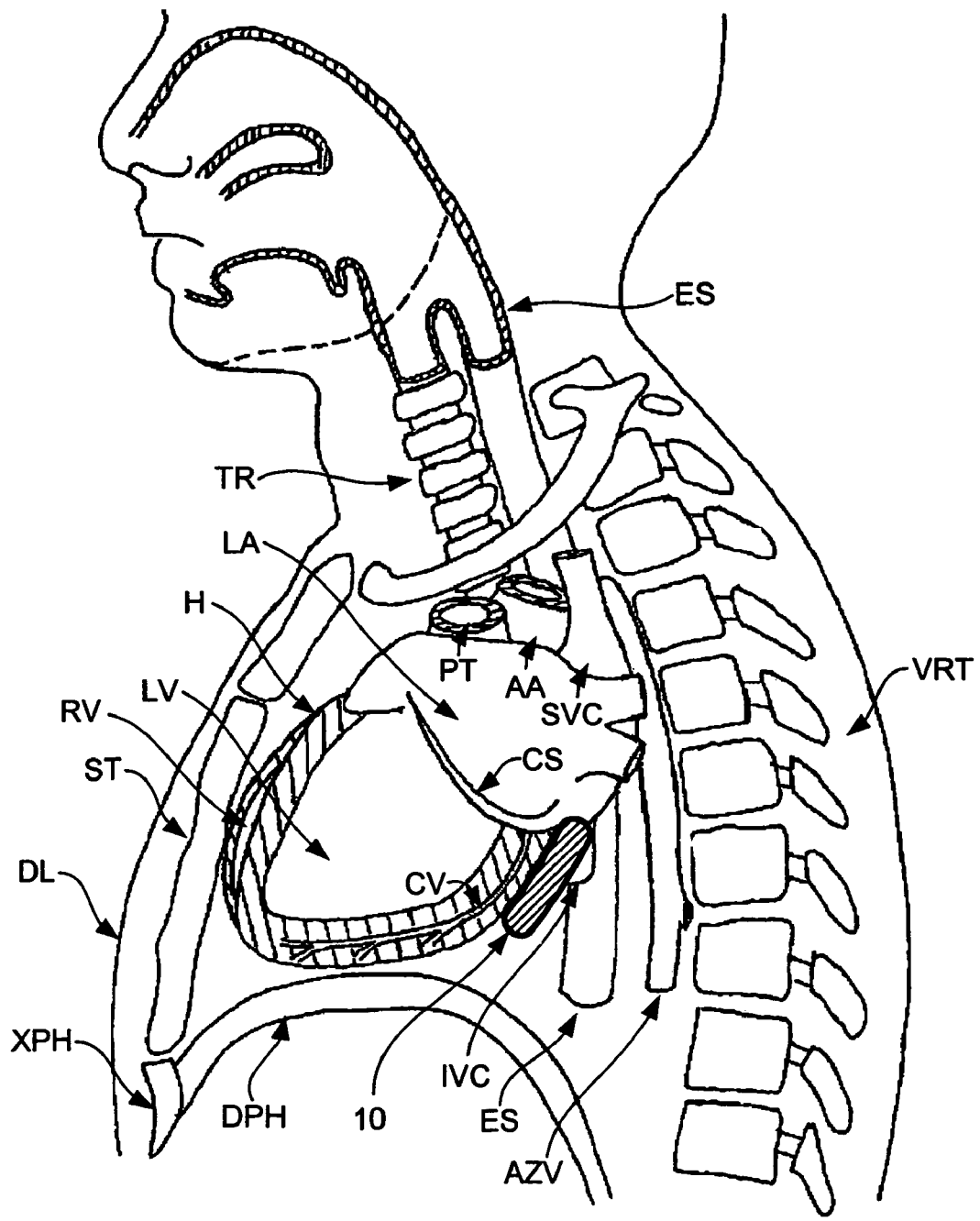
FIGS. 3A-3J are schematic illustrations showing various approaches for implanting space filling devices.

With reference to FIGS. 3A-3J, various approaches for implanting space filling devices 10 are shown. For purposes of illustration, not necessarily limitation, the space filling device 10 may be implanted outside the wall of the heart H adjacent the mitral valve MV to improve valvular function as illustrated in FIG. 3A. The space filling device may be implanted outside the epicardium, such as between the epicardium and pericardium, or between the pericardium and the pleural sac, for example. There are a number of different approaches and techniques for positioning the space filling device 10 as such, and these approaches generally include surgical, transluminal and transthoracic techniques. An example of a suitable surgical technique is conventional open heart surgery similar to that which is performed for coronary artery bypass surgery (CABG) or valve repair, which may be performed on-pump or off-pump. Examples of transluminal and transthoracic approaches are described in more detail with reference to FIGS. 3B-3J. Suitable delivery catheters, guide catheters, guide wires, and other tools are described in more detail with reference to FIGS. 4-9.

Figure 3B:
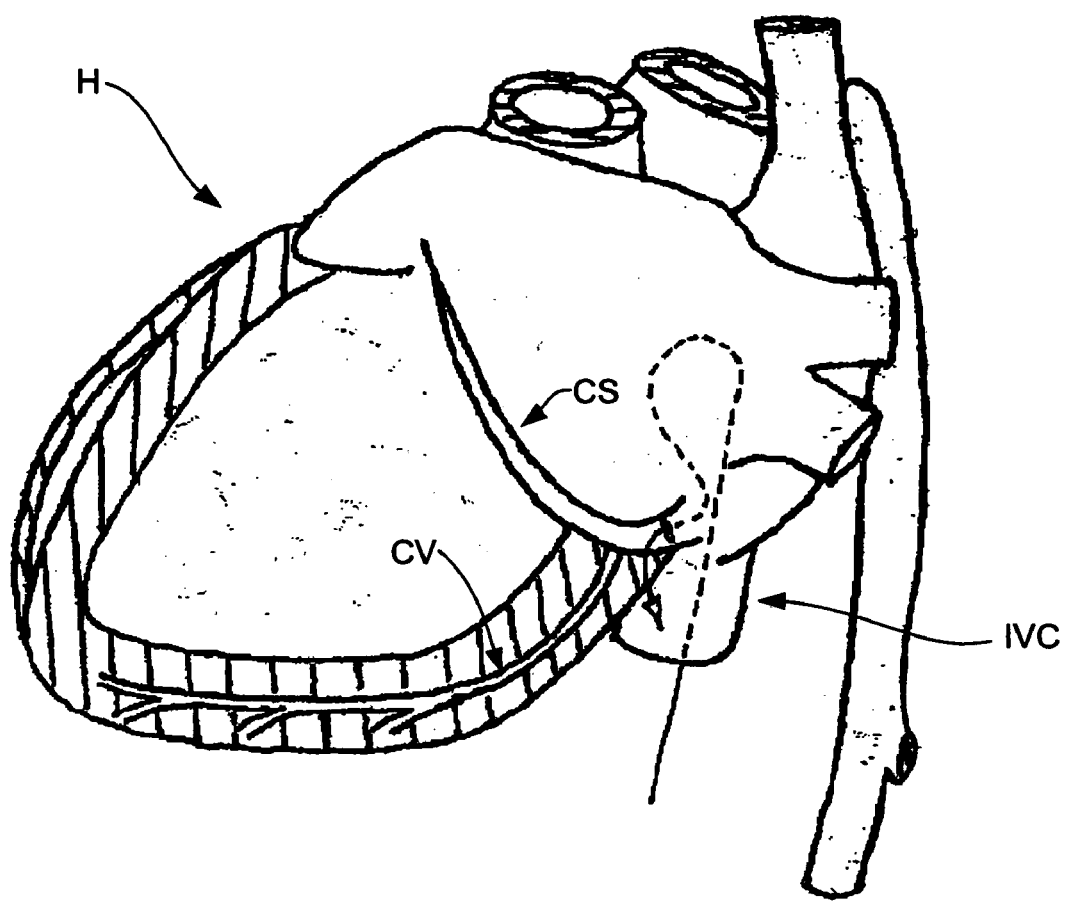

In FIG. 3B, a transluminal approach via the coronary sinus CS is shown as a dashed line with a distal arrow. The coronary sinus CS may be catheterized by, for example, using a guide catheter and guide wire navigated through the inferior vena cava IVC or superior vena cava SVC from a convenient venous access site such as a femoral, brachial or jugular approach. The guide catheter may be navigated into the right atrium RA and the distal end of the guide catheter may be seated in the ostium of the coronary sinus CS. The delivery catheter may be navigated through the guide catheter into the coronary sinus CS, with its distal end positioned near the desired exit point into the pericardial space. The guide wire may be advanced through the delivery catheter, out the distal end of the delivery catheter, and penetrate through the wall of the coronary sinus CS at the exit point. The delivery catheter may be advanced over the guide wire and through the hole in the coronary sinus CS and manipulated to the desired deployment position in the pericardial space adjacent the mitral valve MV or a specific part thereof.

The space filling device 10, which may be predisposed at the distal end of the delivery catheter or advanced to the distal end thereof, is then manipulated into the desired position and expanded. The position of the space filling device 10 may be monitored and confirmed using medical imaging techniques such as radiographic techniques, for example, with radiopaque material incorporated into the space filling device 10 and/or the distal end of the delivery catheter. Upon deployment and expansion of the space filling device, assessment of the position of the space filling device 10 relative to internal mitral valve MV structures such as leaflets AL/PL, papillary muscles PM, and regurgitant jet may be performed with ultrasonic imaging such as trans-esophageal or epicardial echocardiography. These techniques may also be used to refine the position of the space filling device 10 until the desired acute effect is established. Once in the desired position, the space filling device 10 may be detached or otherwise disengaged from the distal end of the delivery catheter, and the delivery catheter, guide wire and guide catheter may be removed. If desired, a catheter or small tube may remain permanently or temporarily attached to the space filling device 10 to selectively adjust the degree of expansion by adding or removing material therefrom.

Figure 3C:
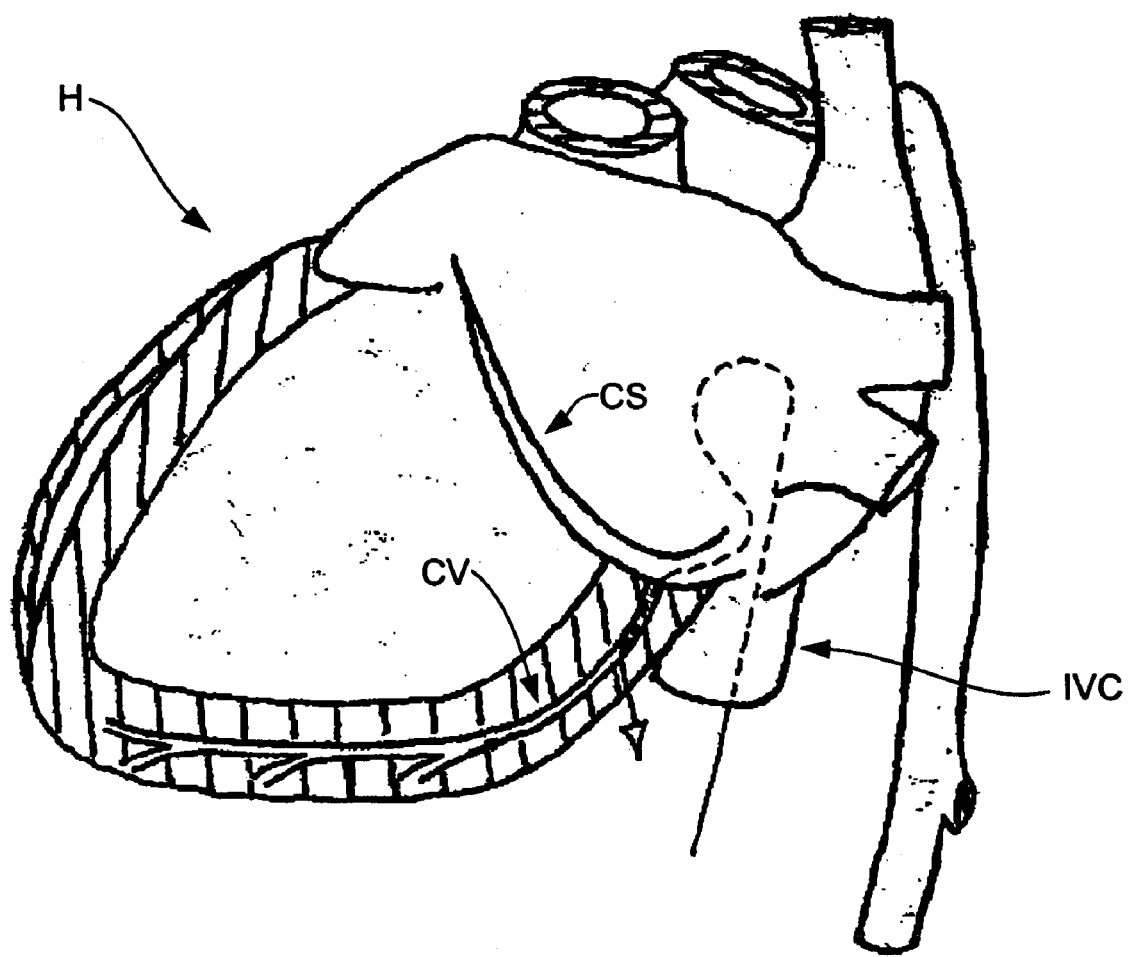

In FIG. 3C, a transluminal approach via a cardiac vein CV is shown as a dashed line with a distal arrow. This approach is similar to the carotid sinus CS approach described above except that the delivery catheter is navigated further through the carotid sinus CS and into a desirable cardiac vein CV near the desired implant site. The cardiac vein CV may be catheterized by, for example, using a guide catheter and guide wire navigated through the inferior vena cava IVC or superior vena cava SVC from a convenient venous access site such as a femoral, brachial or jugular approach. The guide catheter may be navigated into the right atrium RA and the distal end of the guide catheter may be seated in the ostium of the coronary sinus CS. The delivery catheter may be navigated through the guide catheter into the coronary sinus CS, into a cardiac vein CV, with its distal end positioned near the desired exit point into the pericardial space. The guide wire may be advanced through the delivery catheter, out the distal end of the delivery catheter, and penetrate through the wall of the cardiac vein CV at the exit point. The delivery catheter may be advanced over the guide wire and through the hole in the cardiac vein CV and manipulated to the desired deployment position in the pericardial space adjacent the mitral valve MV or a specific part thereof. The remaining steps for implantation may be the same or similar to those described above with reference to FIG. 3B.

Figure 3D:
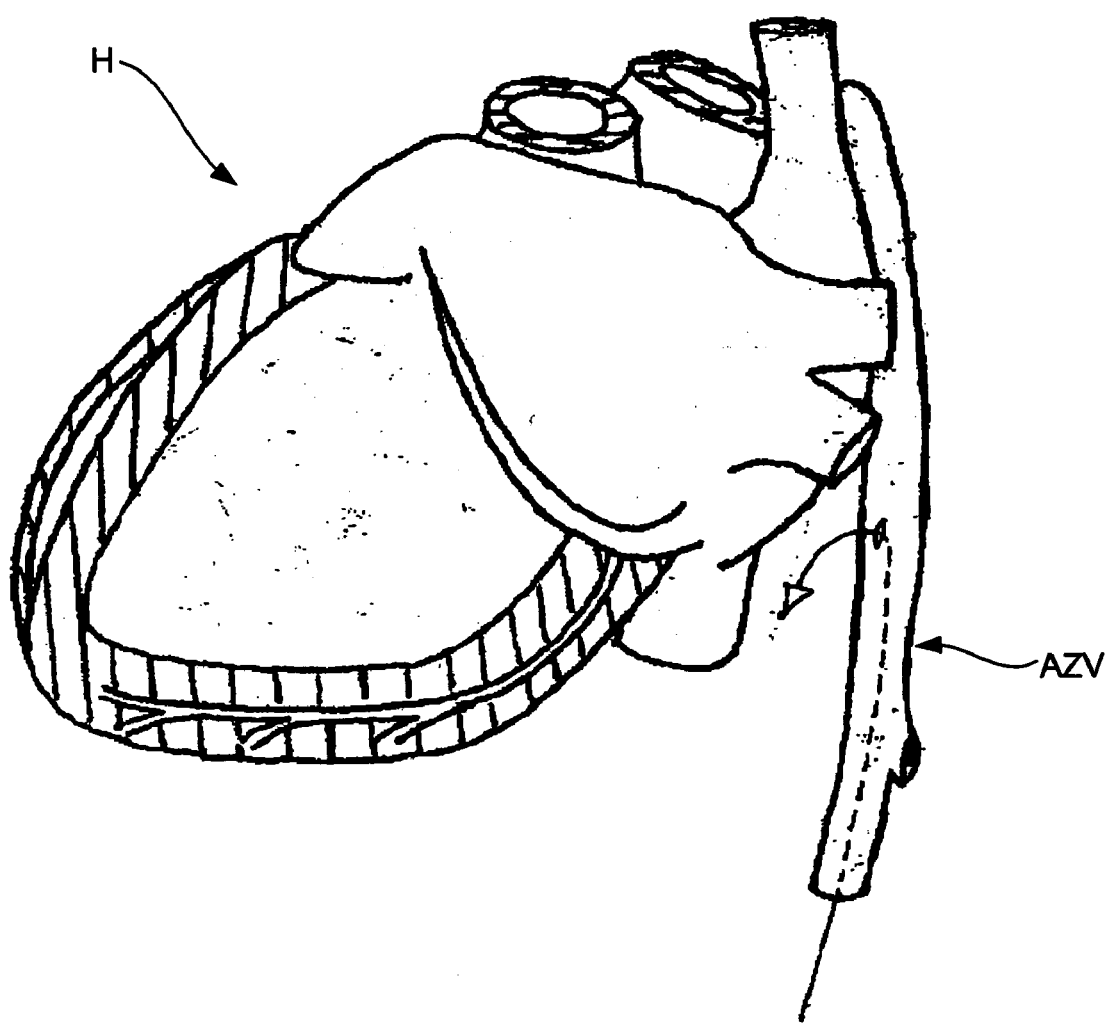

In FIG. 3D, a transluminal approach via the azygos vein AZV is shown as a dashed line with a distal arrow. The azygos vein AZV extends past the posterior aspect of the heart H near the left-right midline as best seen in FIG. 1A. The azygos vein AZV may be catheterized by, for example, using a guide catheter and guide wire navigated through the venous system from a convenient venous access site such as a femoral vein. The guide catheter may be navigated up to and adjacent the desired exit point adjacent the mitral valve MV or a specific part thereof. The delivery catheter may be navigated through the guide catheter until the distal end of the delivery catheter exits the distal end of the guide catheter and is positioned near the desired exit point. The guide wire may be advanced through the delivery catheter, out the distal end of the delivery catheter, and penetrate through the wall of the azygos vein AZV at the exit point. The delivery catheter may be advanced over the guide wire and through the hole in the azygos vein AZV and manipulated to the desired deployment position in the pericardial space adjacent the mitral valve MV or a specific part thereof. The remaining steps for implantation may be the same or similar to those described above with reference to FIG. 3B.

Figure 3E:
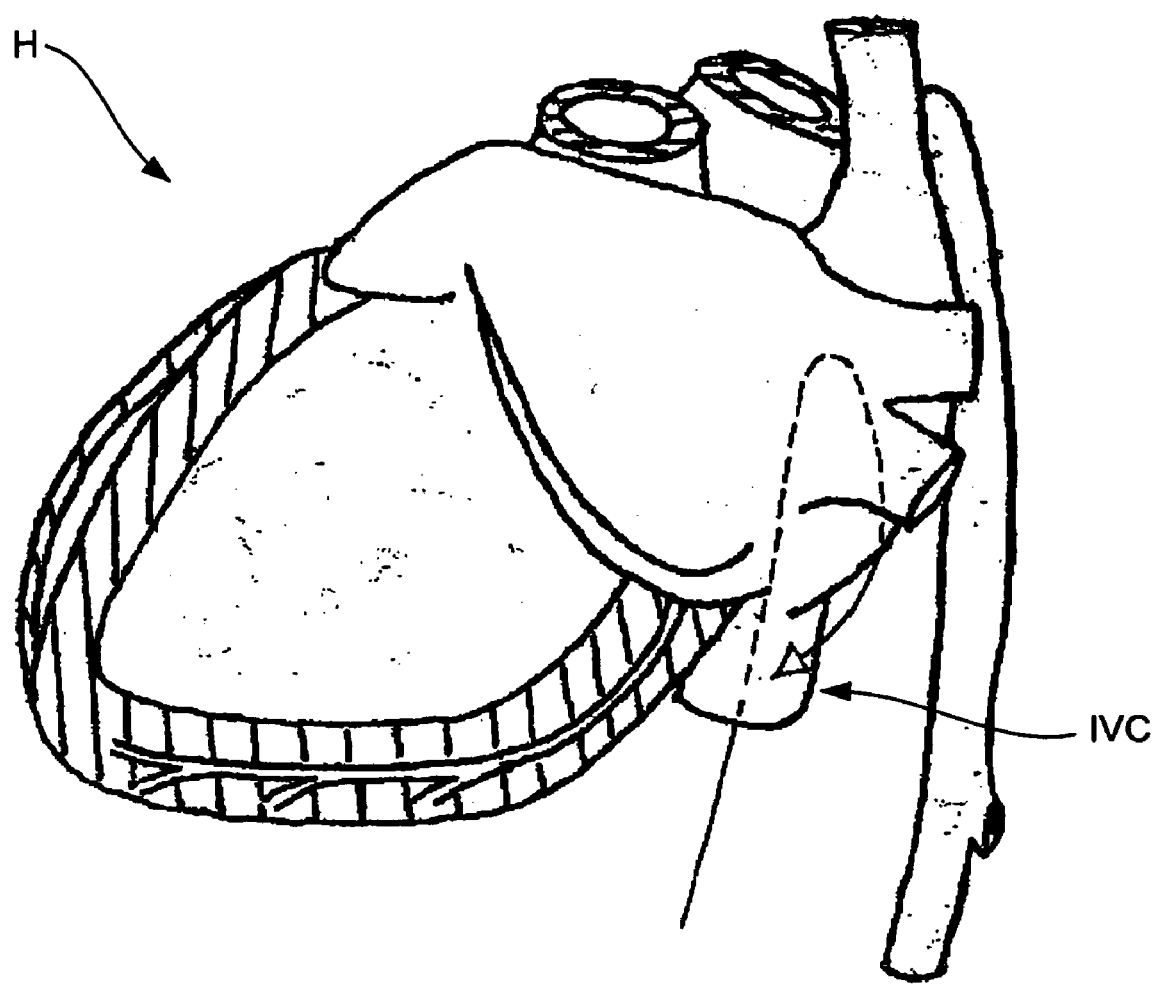

In FIG. 3E, a transluminal approach via the right atrium RA is shown as a dashed line with a distal arrow. The pericardial space may be accessed via the right atrium RA using a percutaneous transatrial technique wherein the right atrium or right atrial appendage is catheterized by, for example, using a guide catheter and guide wire navigated through the inferior vena cava IVC from a convenient venous access site such as a femoral approach. The guide catheter may be navigated into the right atrium or atrial appendage and the guide wire may be used to puncture through the atrial wall to gain access to the pericardial space. The delivery catheter may be advanced over the guide wire and through the hole in the atrial wall and manipulated to the desired deployment position in the pericardial space adjacent the mitral valve MV or a specific part thereof. The remaining steps for implantation may be the same or similar to those described above with reference to FIG. 3B.

Figure 3F:
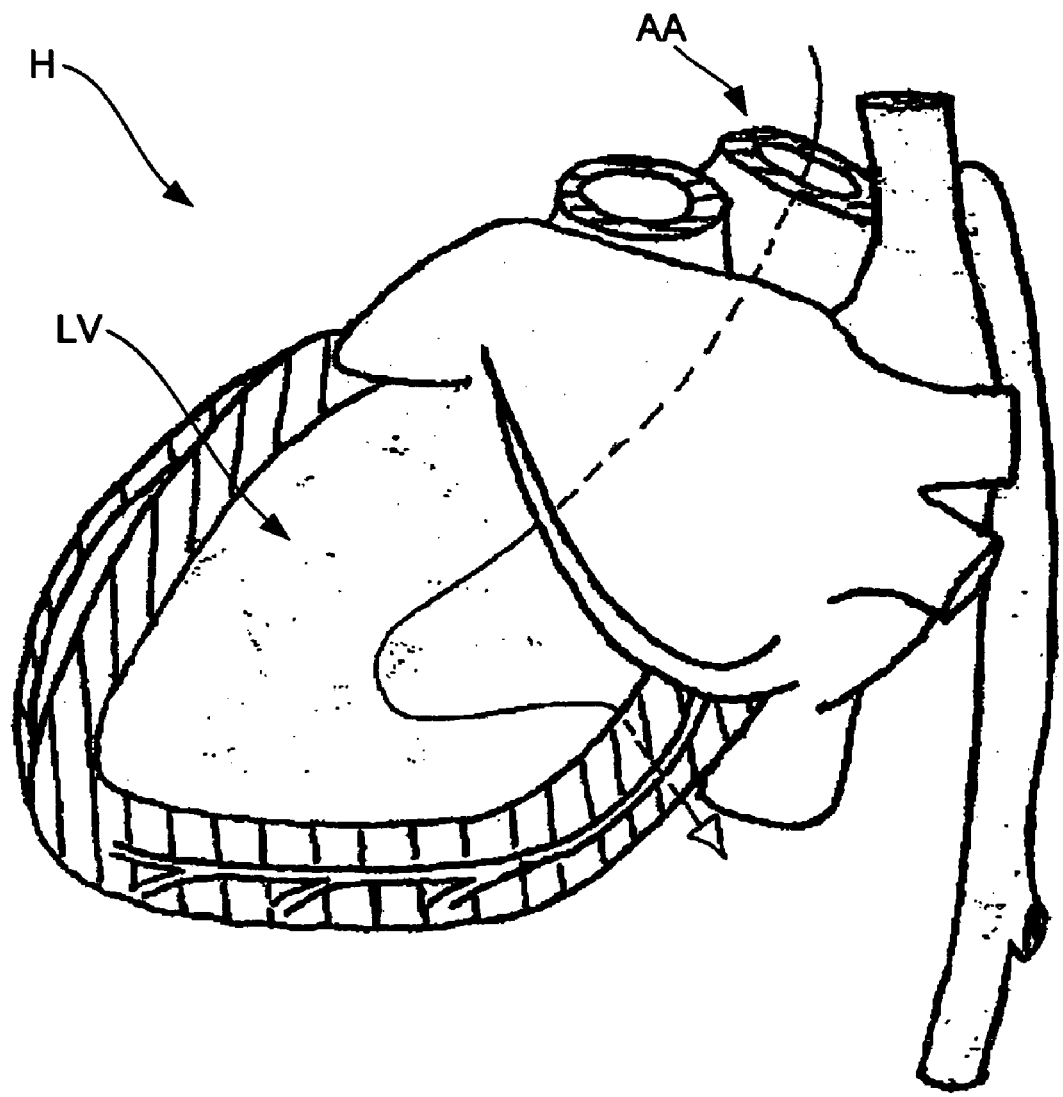

In FIG. 3F, a transluminal approach via the left ventricle LV is shown as a dashed line with a distal arrow. The pericardial space may be access via the left ventricle LV using a percutaneous transventricular technique wherein the left ventricle LV is catheterized by, for example, using a guide catheter and guide wire navigated through the ascending aorta AA from a convenient arterial access site such as a femoral approach. The guide catheter may be navigated into the left ventricle LV and the guide wire may be used to puncture through the ventricular wall to gain access to the pericardial space. The delivery catheter may be advanced over the guide wire and through the hole in the ventricular wall and manipulated to the desired deployment position in the pericardial space adjacent the mitral valve MV or a specific part thereof. The remaining steps for implantation may be the same or similar to those described above with reference to FIG. 3B.

Figure 3G:
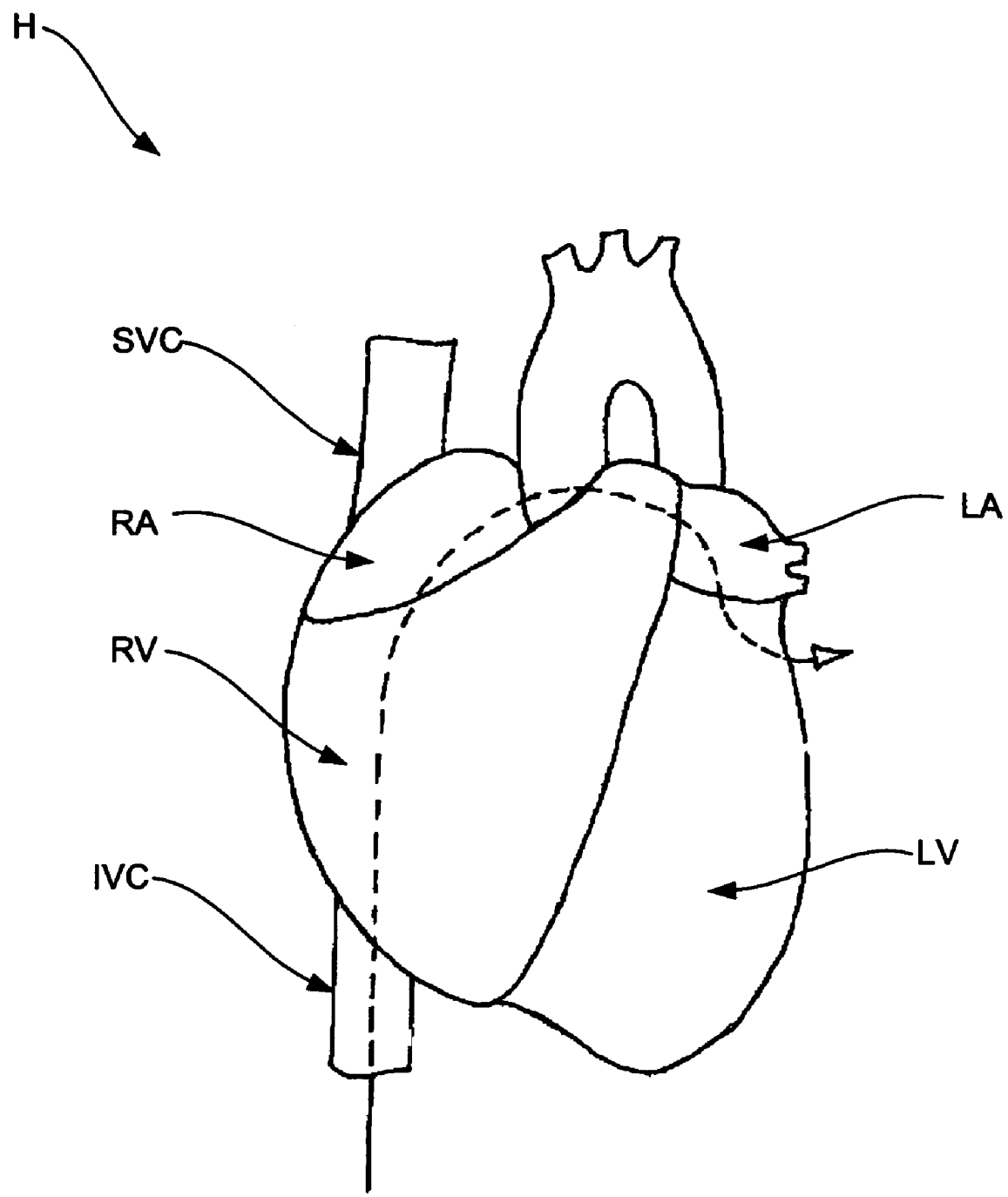

In FIG. 3G, another transluminal approach via the left ventricle LV is shown as a dashed line with a distal arrow. The pericardial space may be access via the left ventricle LV using a percutaneous transventricular technique wherein the left ventricle LV is catheterized by, for example, using a guide catheter and guide wire navigated through the inferior vena cava IVC from a convenient venous access site. The guide wire may be navigated into the right atrium RA, through the atrial septum, into the left atrium LA, through the mitral valve MV, into the left ventricle LV, and punctured through the left ventricular wall to gain access to the pericardial space. The delivery catheter may be advanced over the guide wire and through the hole in the ventricular wall and manipulated to the desired deployment position in the pericardial space adjacent the mitral valve MV or a specific part thereof. The remaining steps for implantation may be the same or similar to those described above with reference to FIG. 3B.

Figure 3H:
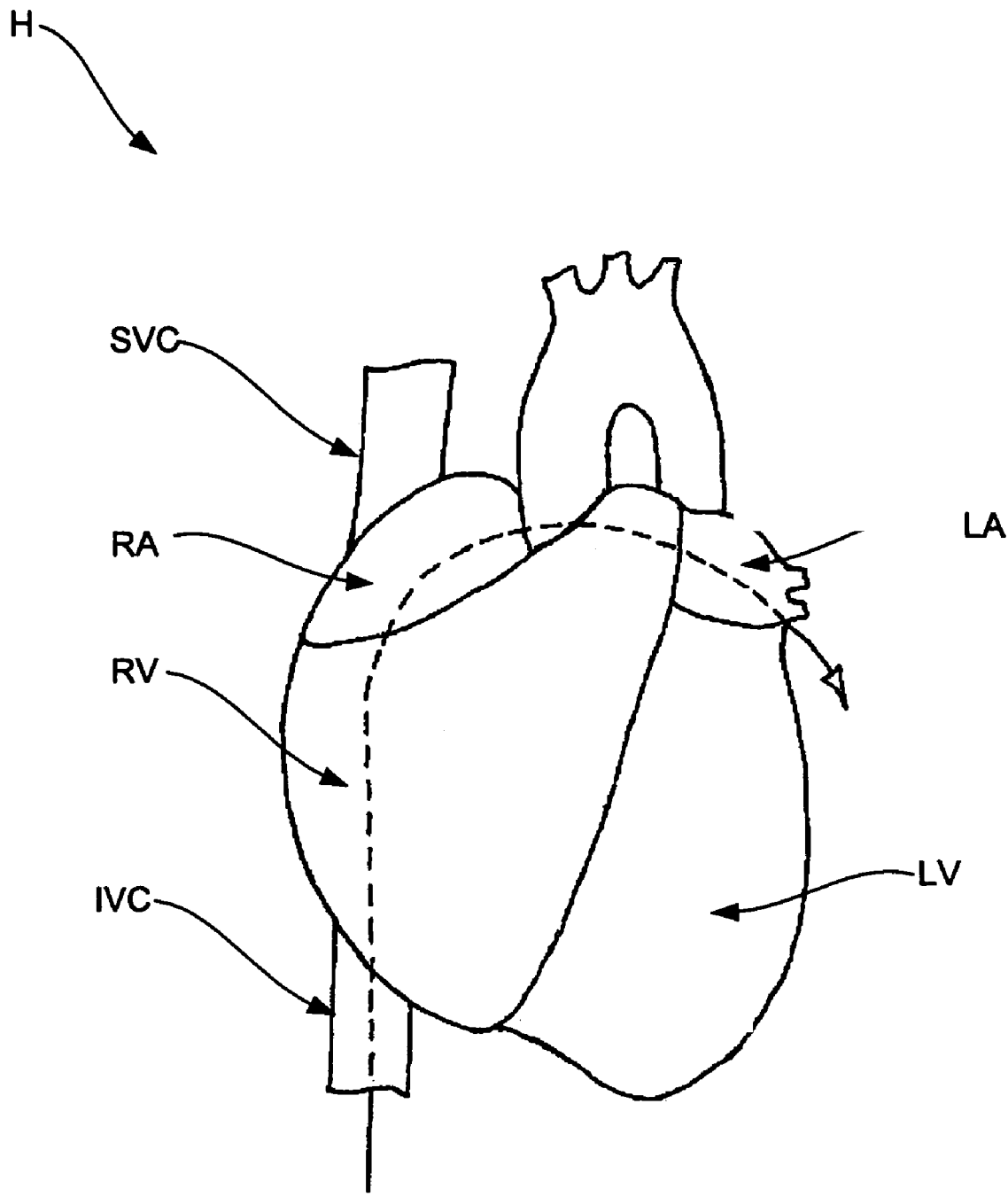

In FIG. 3H, a transluminal approach via the left atrium LA is shown as a dashed line with a distal arrow. The pericardial space may be access via the left atrium LA using a percutaneous transatrial technique wherein the left atrium LA is catheterized by, for example, using a guide catheter and guide wire navigated through the inferior vena cava IVC from a convenient venous access site. The guide wire may be navigated into the right atrium RA, through the atrial septum, into the left atrium LA, and punctured through the left atrial wall to gain access to the pericardial space. The delivery catheter may be advanced over the guide wire and through the hole in the atrial wall and manipulated to the desired deployment position in the pericardial space adjacent the mitral valve MV or a specific part thereof. The remaining steps for implantation may be the same or similar to those described above with reference to FIG. 3B.

Figure 3I:
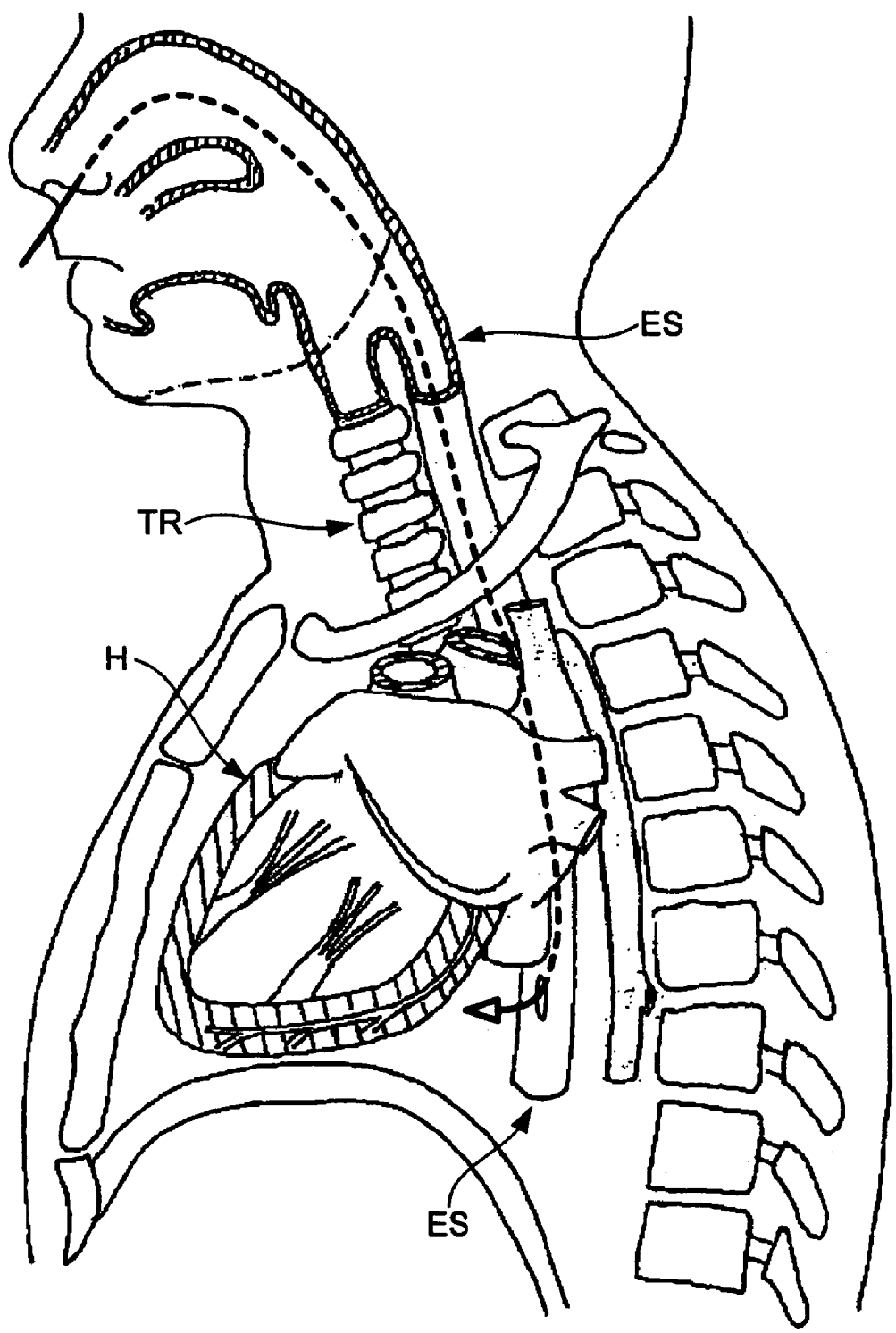

In FIG. 3I, a transluminal approach via the esophagus ES is shown as a dashed line with a distal arrow. The esophagus ES extends past the heart H near the posterior aspect of the right atrium as best seen in FIG. 1A. Because the esophagus ES does not provide a sterile environment, as isolation catheter such as the catheter described with reference to FIG. 9 may be used to isolate a portion of the esophageal lumen and establish a sterile environment. The isolation catheter may be inserted through nasal passage, past the pharynx, and into the esophagus ES as shown by the dashed line in FIG. 3I. Alternatively, the isolation catheter may be inserted into the esophagus ES via the mouth. The distal portion of the isolation catheter may be positioned adjacent the heart H at the level of the mitral valve MV as confirmed by a suitable visualization techniques such as ultrasonic imaging (e.g., trans-esophageal, trans-thoracic or epicardial echocardiography). Once in the desired position, the balloons of the isolation catheter may be inflated and the space between the balloons may be flushed with a suitable sterilizing wash. Having established an isolated sterile environment between the balloons of the isolation catheter, a guide wire may be advanced through the isolation catheter exiting between the balloons and puncturing the esophageal wall at the desired exit point. The delivery catheter may be advanced over the guide wire and through the hole in the esophageal wall and manipulated to the desired deployment position in the pericardial space adjacent the mitral valve MV or a specific part thereof. The remaining steps for implantation may be the same or similar to those described above with reference to FIG. 3B.

Figure 3J:
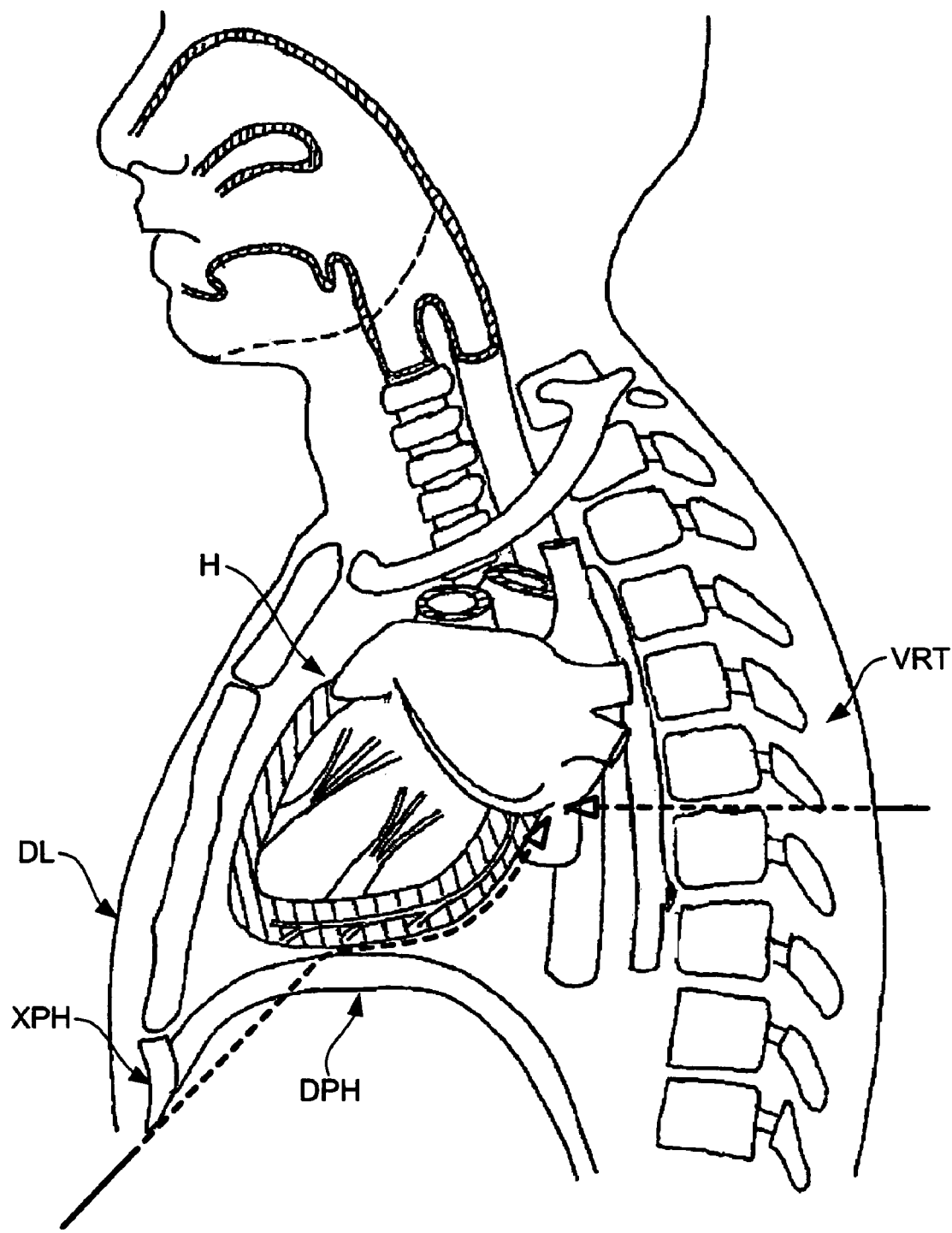

In FIG. 3J, two transthoracic approaches are shown as dashed lines with a distal arrow. The anterior approach may comprise a subxiphoid approach to establish access to the pericardial space similar to the techniques described by Schmidt et al. in U.S. Pat. No. 6,206,004, the entire disclosure of which is incorporated herein by reference. The posterior approach may utilize similar tools and techniques to access the pericardial space from the back between the ribs and extending into the thoracic cavity. Once pericardial access is established with, for example, a thoracic guide catheter used in such techniques, a delivery catheter may be advanced over or together with a guide wire and manipulated to the desired deployment position in the pericardial space adjacent the mitral valve MV or a specific part thereof. The remaining steps for implantation may be the same or similar to those described above with reference to FIG. 3B.

Description of Delivery and Ancillary Tools

With reference to FIG. 4, a schematic plan view of a delivery catheter 20 and a guide wire 40 is shown for use in delivering a space filling device 10 by the transluminal techniques described above, for example. Delivery catheter 20 includes an elongate shaft 22 that is sized appropriately as a function of the delivery approach, both in terms of the size of the lumen and the distance from the access point to the deployment point. As seen in FIG. 5A, the elongate shaft 22 may comprise a coaxial over-the-wire design with an outer tube 32 coaxially disposed about an inner tube 34. The inner tube may define a guide wire lumen 35 and the annular space between the outer tube 32 and the inner tube 34 may define an inflation lumen 33. Alternatively, as seen in FIG. 5B, the elongate shaft 22 may comprise an innerless, semi-movable wire, or fixed-wire design with the outer tube 32 coaxially disposed about the guide wire 40, and a distal (movable, semi-movable or fixed) fluid seal provided between the distal end of the outer tube 32 and a distal portion of the guide wire 42. In this alternative design, the outer tube 32 may define a combined guide wire lumen 35 and inflation lumen 33. In both designs, the outer tube 32 includes an opening (not shown) to establish fluid communication with the interior 12 of the space filling device 10.

A manifold 24 may be connected to the proximal end of the elongate shaft 22 and may include an inflation lumen arm 26 and a through lumen arm 28. The inflation lumen arm 26 is in fluid communication with the inflation lumen 33 extending through the shaft 22 and the interior 12 of the space filling device 10. The through lumen arm 28 provides access for the guide wire 40 to extend into the guide wire lumen 35 through the shaft 22 and through the space filling device 10. The inflation lumen arm 26 may be connected to an inflation device or other source of filler material such that material may be selectively added to or removed from the interior 12 defined by wall 14 of the space filling device 10.

The space filling device 10 may be releasably connected to a distal portion of the shaft 22 by a release mechanism 30 (shown schematically). The release mechanism 30 may comprise a wide variety of forms known in the art related to detachable balloons and detachable coils. The release mechanism 30 may be actuated at the proximal end of the catheter 20 by an appropriate means depending on the type of release mechanism utilized. The release mechanism 30 operates to secure the space filling device 10 to the distal portion of the shaft 22 during delivery until the space filling device 10 is the desired deployment position. Once the space filling device is in the desired position and expanded, the release mechanism 30 may be actuated to sever the connection between the delivery catheter 20 and the space filling device 10.

The guide wire 40 may have sufficient length to extend through the delivery catheter, and sufficient flexibility and column strength to facilitate manipulation, navigation and tissue puncture capabilities. The size and shape of the distal tip 42 of the guide wire 40 may be selected as a function of what lumen need to be navigated and what tissue needs to be penetrated. For example, the distal tip 42 may comprise a rounded tip having a diameter similar to a coronary guide wire to enable navigation through the vasculature and pericardial space, but with sufficient stiffness to puncture venous walls and atrial walls. Alternatively, the distal tip 42 may have a smaller diameter or may be sharpened to puncture ventricular walls, esophageal walls, etc.

Figure 7A:
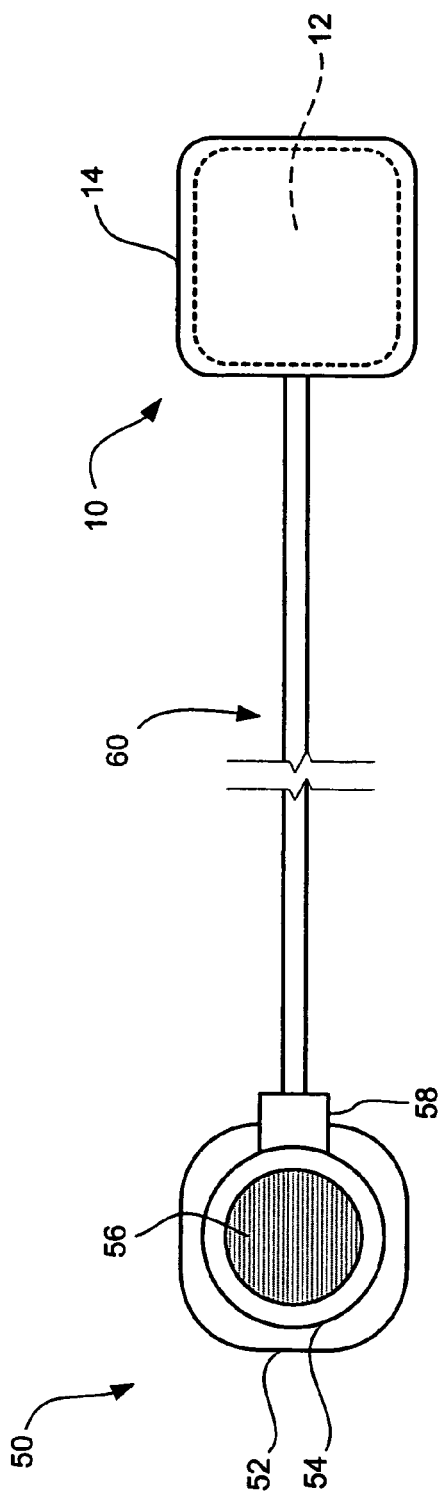
FIGS. 7A and 7B are schematic top and side views of a transdermal access port connected to a space filling device by a flexible tube.
Figure 7B:
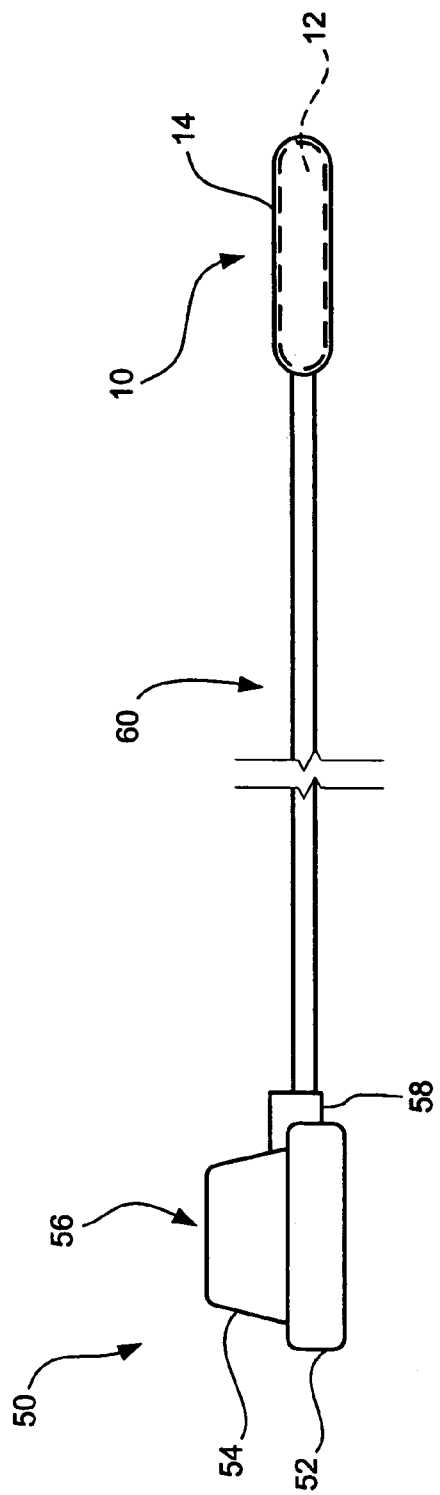

With reference to FIGS. 7A and 7B, schematic top and side views of a transdermal access port 50 connected to a space filling device 10 by a flexible catheter 60. The transdermal access port 50 may be used to selectively add or remove material to or from (e.g., inflate or deflate) the space filling device 10 after the device 10 has been deployed and the delivery procedure has been completed. For example, if the desired acute effect is achieved during deployment of the space filling device 10, but thereafter the effect diminishes or otherwise changes in an undesirable way, it may be desirable to modify the size and/or shape of the space filling device 10 by selectively adding or removing material form the device 10 using the transdermal access port 50.

The transdermal access port 50 generally includes a base housing 52 and a reservoir housing 54 containing a reservoir (not visible) therein. A septum 56 is disposed over the top of the reservoir in the housing 54 and permits a needle to be inserted into the reservoir. The catheter 60 is connected to the reservoir housing 54 at strain relief 58 and is in fluid communication with the reservoir therein. The transdermal access port 50 may be implanted just below the dermal layer DL at a convenient access point such as in the pectoral region. The catheter 60 extends from the subdermal location of the transdermal access port 50 to the space filling device 10 located adjacent the heart. With this arrangement, a needle may be used to inject fluid, for example, through the septum 56 and into the reservoir of the transdermal access port 50. From the reservoir of the transdermal access port 50, the fluid passes through the flexible catheter 60 and into the interior 12 of the space filling device 10 to increase its size and/or shape. In a similar manner, a needle may be used to withdraw fluid from the interior 12 of the space filling device 10 to decrease its size and/or shape. The catheter 60 may be connected to the space filling device 10 prior to deployment thereof and snaked to the transdermal access port 50 via the delivery path defined by the delivery catheter or via an alternative route to the transdermal access port 50, which may be surgically placed in a subdermal pocket. Alternatively, the catheter 60 may be connected to the space filling device 10 after deployment thereof.

Figure 8:
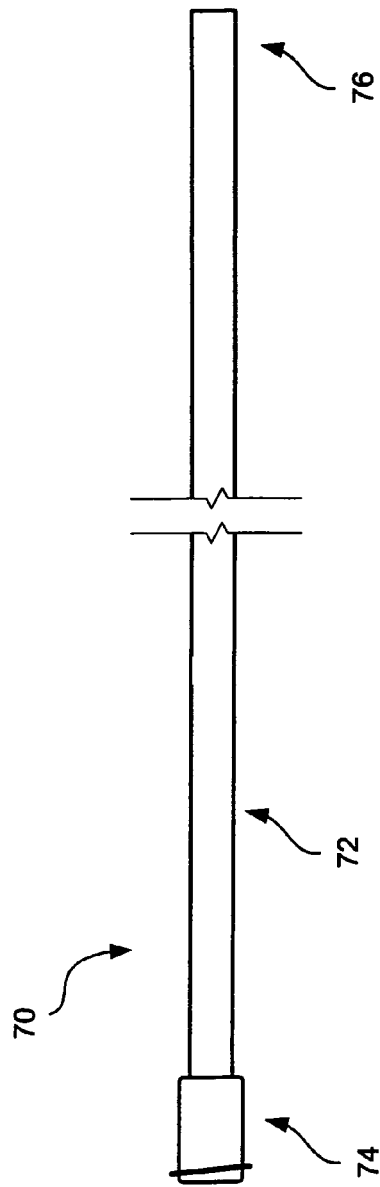
FIG. 8 is a schematic plan view of a guide catheter for use in delivering space filling devices by transluminal techniques.

With reference to FIG. 8, a schematic plan view of a guide catheter 70 is shown, for use in delivering a space filling device 10 by transluminal techniques, for example. The guide catheter 70 includes an elongate shaft 72 that is sized appropriately as a function of the delivery approach, both in terms of the size of the lumen and the distance from the access point to the deployment point. A hub 74 may be connected to the proximal end of the shaft 72 to facilitate insertion of a delivery catheter and/or guide wire, and to permit connection to a syringe for infusion of fluids such as radiopaque media. The construction of the shaft 72 may be conventional, such as a multilayered design with composite braid and polymeric layers. The distal portion 76 of the shaft 72 may be curved with one or more curves in two or three dimensions to facilitate navigation and seating in the luminal path chosen. By way of example, not limitation, the guide catheter 70 may comprise a commercially available 8 French multipurpose guide catheter.

Figure 9:
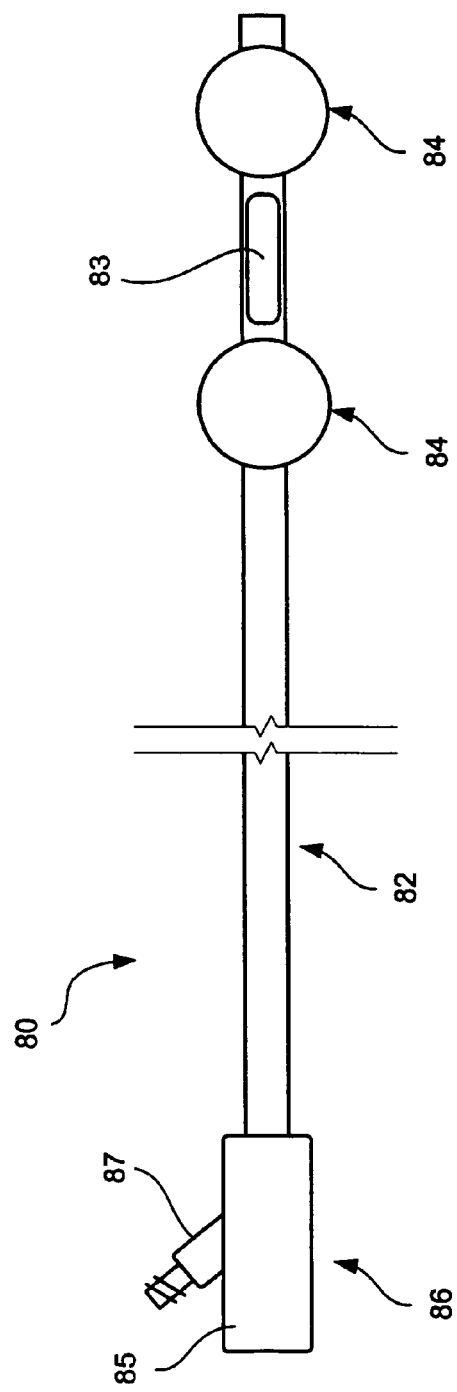
FIG. 9 is a schematic plan view of an isolation catheter for use in delivering space filling devices by transluminal techniques.

With reference to FIG. 9, a schematic plan view of an isolation catheter 80 is shown, for use in delivering a space filling device 10 by transluminal techniques, such as a transesophageal approach. The isolation catheter 80 includes an elongate shaft 82 that is sized appropriately as a function of the delivery approach, both in terms of the size of the lumen and the distance from the access point to the deployment point. For example, for a transesophageal approach, the shaft 82 may have a diameter sized to fit into the esophagus ES and a length sufficient to extend from the nose or mouth to a point adjacent the heart H. The shaft 82 includes a through lumen (not visible) for passage of a delivery catheter and/or guide wire, and a distal window or opening 83 through which the space filling member 10, the delivery catheter and/or the guide wire may exit the catheter 80 between two balloons 84, and through which a sterilizing wash solution may be flushed to aspirate the region between the balloons 84. The shaft 82 also includes an inflation lumen (not visible) to selectively inflate and deflate the balloons 84. Upon inflation in the luminal passage (e.g., esophageal lumen), the balloons 84 define an isolation zone therebetween that may be sterilized and isolated from the remainder of the passage. A manifold 86 may be connected to the proximal end of the shaft 82, and may include an inflation lumen arm 87 in fluid communication with the inflation lumen in the shaft 82 and a through lumen arm 85 to provide access to the through lumen in the shaft 82 and window 83.

With reference to FIGS. 23A and 23B, side and top views, respectively, of anchor catheter 2300 are illustrated. Anchor catheter 2300 is particularly useful for delivering space filling devices by transthoracic techniques. Anchor catheter 2300 includes an elongate tubular shaft 2302 comprising a relatively rigid material such as stainless steel, NiTi, a braided composite. The elongate shaft 2302 may be straight or gently curved depending on the approach (subxiphoid or posterior). A suction cup 2304 may be connected to the distal end of the shaft 2302. The suction cup 2304 defines an interior 2308, and may have an open top and bottom, or an open bottom and closed top. For example, the suction cup 2304 may have an open top and bottom facing both the pericardium and epicardium, or an open bottom facing the epicardium and a closed top facing the pericardium.

The interior 2308 of the suction cup 2304 is in fluid communication with a vacuum lumen extending through the shaft 2302 to hub 2306, which may be connected to a vacuum source (not shown). A flexible guide wire 2320 extends alongside the shaft 2302, with its distal end connected to the suction cup 2304 and its proximal end free. A guide wire tube 2310 may extend through the suction cup 2304 to slidably accommodate pericardial space guide wire 2330 shown in phantom. A radiopaque marker 2312 may be disposed about the guide wire tube 2310 to facilitate visualization by radiography.

Pericardial space guide wire 2330 may be delivered into the pericardial space using a subxiphoid transthoracic cardiac access technique similar to that which is described by Schmidt et al. in U.S. Pat. No. 6,206,004, the entire disclosure of which is incorporated herein by reference. The pericardial space guide wire 2330 provides access to the pericardial space, but typically has a free distal end and therefore may not be easily positioned or anchored in the desired location. Accordingly, the anchor catheter 2300 may be advanced over the pericardial space guide wire 2330, manipulated to the desired implant location using semi-rigid shaft 2302, and anchored in place using vacuum. Application of vacuum to suction cup 2304 effectively anchors the distal end of the catheter 2300 to the heart wall and permits delivery catheter 1900 (described hereinafter) to be advanced thereover.

Description of Design Alternatives for Space Filling Devices

With reference to FIGS. 10-22, schematic illustrations of various design alternatives of space filling devices 10 are shown. In FIGS. 10-15, a bottom view is shown in Figures labeled "A" and a side view (cross sectional in some) is shown in Figures labeled "B". The bottom view generally corresponds to the surface or surfaces facing the wall of the heart H and may lie directly against the epicardium, for example. The side view may represent a superior/inferior view, and/or a lateral view, depending on the selected orientation of the device. The size, shape and orientation of the space filling devices 10 may be selected as a function of the implant site, such as the anatomical features associated with the implant site, and as a function of the desired effect(s) on valve function. The design alternatives schematically illustrated in FIGS. 10-17 are given by way of example, not limitation, and may be used individually or collectively.

Each space filling device 10 described herein may have virtually any desired size, shape or configuration to meet the particular clinical requirements and to have the desired clinical effect(s) as described previously, some of which have been illustrated in FIGS. 1B-1D, and variations of which are described with reference to FIGS. 10-17. Generally, the space filling device may comprise a single large mass or single large protrusion to uniformly apply force to the heart wall and to avoid focused compression of the coronary arteries and cardiac veins. Alternatively, the space filling device 10 may have a relatively small contact area defined by one or a plurality of protrusions selected and positioned to establish localized contact with the heart wall while avoiding contact with and compression of the coronary arteries and cardiac veins.

In FIGS. 10A and 10B, the space filling device 1010 includes a base 16 defining a wall 14 and an interior 12. A single circular protrusion 18 extends from the base 16, which may be in fluid communication therewith. The base 16 and/or the protrusion 18 may be expanded to the desired size and shape. The base 16 may include a securement as described hereinafter, such as a tissue in-growth promoting surface 17.

In FIGS. 11A and 11B, the space filling device 1110 is similar to device 1010 described above except that a plurality (e.g., two, three or more) of circular protrusions 18 extend from the base 16. This embodiment illustrates that any suitable number of protrusion(s) 18 may be utilized.

In FIGS. 12A and 12B, the space filling device 1210 is similar to device 1010 except that a single oblong protrusion 18 extends from the base 16. This embodiment illustrates that the protrusion(s) 18 may assume a wide variety of geometries, including circular and non-circular geometries.

In FIGS. 13A and 13B, the space filling device 1310 the space filling device 1210 is similar to device 1010 except that one or more elongate protrusions 18 are integrally formed with and extend from both sides of the base 16. In addition, reinforcement strips 19 may be disposed at the apex of the protrusions 18 to enhance rigidity thereof. This embodiment illustrates that the protrusions 18 may be integrally formed with the base 16, and/or may extend from both sides of the base 16, and/or may be selectively reinforced.

In FIGS. 14A and 14B, the space filling device 1410 is similar to device 1310 except that the protrusion 18 includes a reinforcement structure 19 (e.g., 2-dimensional or 3-dimensional coil or stent) disposed in the interior 12 thereof to enhance the hoop strength of the protrusion 18. The reinforcement structure 19 disposed in the elongate protrusion 18 illustrates that the hoop strength or holding power of the protrusion(s) 18 may be increased by mechanical means.

In FIGS. 15A and 15B, the space filling device 1510 is similar to device 1010 except that the device 1510 comprises one or more discrete protrusions 18. This embodiment illustrates that the space filling device 1510 may comprise one or more individual and separate protrusions 18 used collectively, which may not define a discrete base portion and a discrete protrusion portion.

Figure 16C:
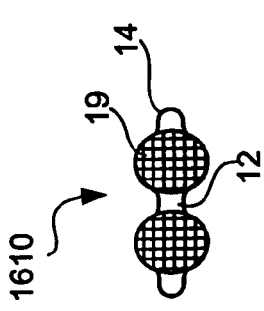
Figure 16F:
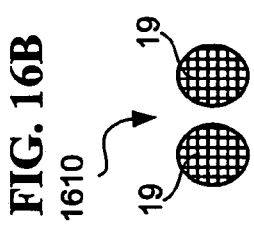
Figure 16B:
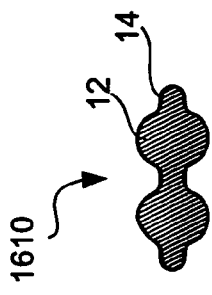
Figure 16E:
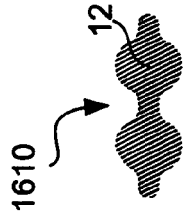
Figure 17B:
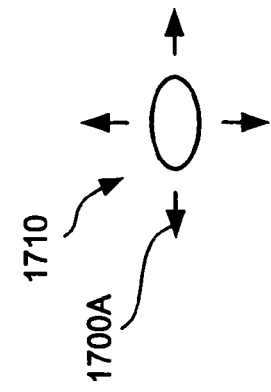
Figure 16A:
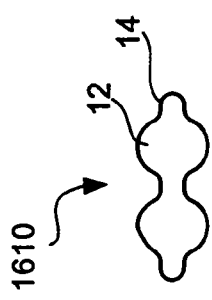
Figure 16D:
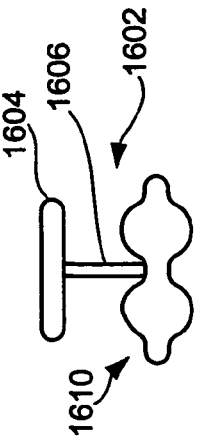
Figure 17A:
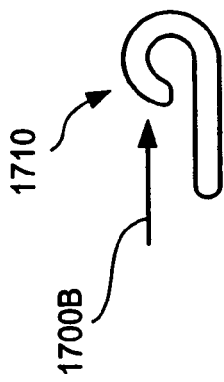

Each space filling device 10 described herein may be expanded or filled by different materials and/or structures, each of which may dictate a different construction of the device 10 as illustrated by the following discussion with reference to FIGS. 16A-16F which schematically illustrate different embodiments of a space filling device 1610. The space filling device 1610 may include an interior 12 defined by wall 14, wherein the interior 12 is filled by a fluid as shown in FIG. 16A. The fluid may remain a liquid (e.g., saline) or a gas (e.g., carbon dioxide) as shown in FIG. 16A, or may comprise or cure into a solid or semi-solid (e.g., gel, expandable foam, sponge, PVA, collagen) as shown in FIG. 16B. In addition or in the alternative, a mechanical structure 19 such as a stent or coil may be placed in the interior 12 as shown in FIG. 16C. To the extent that the wall 14 is not necessary to contain the solid filler material, the device 1610 may have dissolvable walls or may not have walls at all as shown in FIG. 16D. Similarly, to the extent a mechanical structure 19 such as a stent or coil is used, the device 1610 may not require walls as shown in FIG. 16E, and the device 1610 may simply comprise the mechanical structure 19 itself.

In addition, each of the space filling devices 10 may include a means to secure itself to the heart H wall and/or other surrounding tissue. The securement may comprise tines, screws, sutures, or other structural anchors, and/or the securement may comprise a material (e.g., Dacron fabric) that promotes tissue in-growth. The securement may be remotely activated. For example, the securement may comprise curled wires disposed on either side of the space filling device, wherein the wires curl into the heart wall as they are advanced out of a catheter lumen. The securement may selectively anchor to some tissue while remaining free of other tissue. For example, the securement may anchor to the epicardium and/or myocardium, while remaining free of the pericardium. It has been observed that the epicardium is a relatively tough tissue, thus providing a good anatomical structure to secure the space filling device 10.

In the embodiments described with reference to FIGS. 10-15, the securement is shown as a tissue in-growth promoting surface on the bottom, and a smooth surface on the top, thus establishing, for example, a secure connection to the epicardium while remaining free of the pericardium. In the embodiment shown in FIG. 16F, the device 1610 includes an transmyocardial securement 1602 having an intra-chamber anchor pad 1604 and a connection member 1606. The intra-chamber pad 1604 resides within a chamber (e.g., left ventricle LV) of the heart H, and the connection member 1606 extends through the heart wall (endocardium, myocardium and epicardium) to the space filling device 1610 disposed outside the heart wall. The transmyocardial securement 1602 is particularly suited for the transventricular approach described previously.

Each space filling device 10 described herein may be expandable between a relatively small delivery configuration and a relatively large deployed configuration. The smaller delivery configuration permits the device 10 to be low profile to facilitate advancement through catheter lumens in the various transluminal approaches described herein. For example, the space filling device 1710 may be expanded radially as shown by arrows 1700A in FIG. 17A, or unfurled as shown by arrow 1700B in FIG. 17B. Radial expansion may be appropriate when the device 1710 is constructed of highly elastic materials (e.g., silicone rubber, latex, elastomeric polymers, etc.) and unfurling may be appropriate when the device 1710 is constructed of relatively inelastic materials (e.g., PET, HDPE, PTFE, SST, Nitinol, etc.).

Figure 18A:
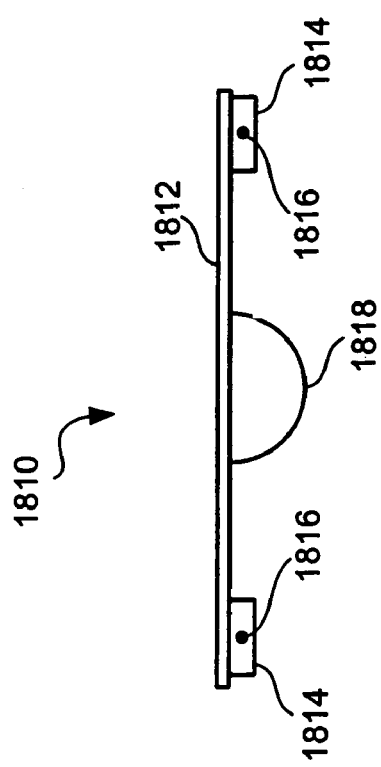
Figure 18B:
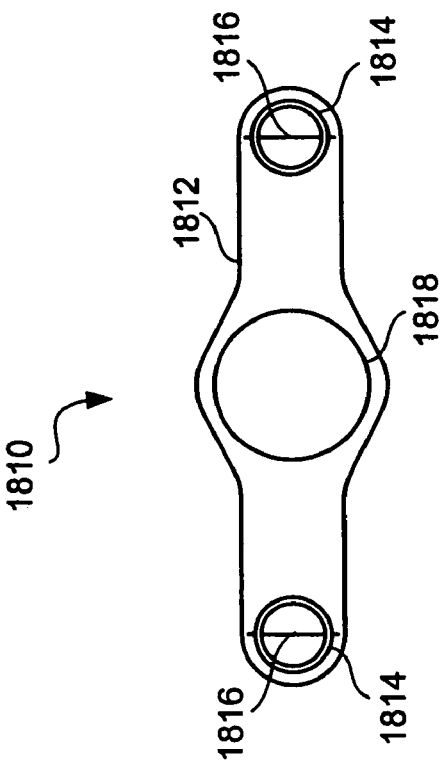

In FIGS. 18A and 18B, side and bottom views, respectively, are shown of space filling device 1810. Space filling device 1810 includes a base 1812 which may comprise, for example, a flexible polymer sheet having resistance to elongation. Two or more suction cups 1814 are connected to opposite ends of the base 1812. The suction cups 1814 have an open bottom portion, with the top portion thereof sealing connected to the base 1812. One or more pins 1816 extend through and across each of the suction cups 1814. The pins 1816 may be inserted and locked in holes defined in the walls of the suction cups 1814. A inflatable and deflatable balloon 1818 is connected to and extends from the bottom of the base 1812. The balloon 1818 may be filled with a variety of materials as described previously.

Figure 19:
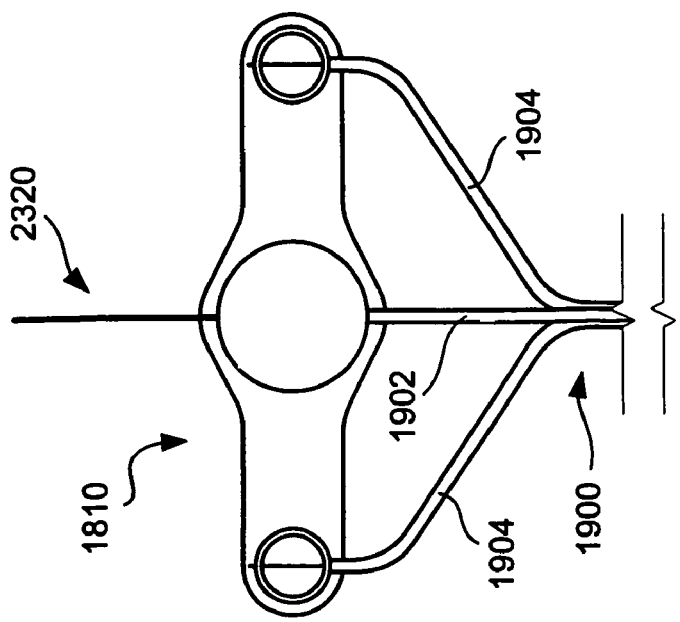

In FIG. 19, a bottom view of a delivery catheter 1900 connected to the space filling device 1810 is shown. Delivery catheter 1900 includes an inflation tube 1902 releasably connected to and in fluid communication with the balloon 1818. Inflation tube 1902 includes an inflation lumen extending therethrough, and may include a guide wire lumen for advancement over guide wire 2320 as shown and described with reference to FIGS. 23A and 23B. The proximal end (not shown) of the inflation tube 1902 may be connected to an inflation device to selectively inflate and deflate the balloon 1818. Delivery catheter 1900 also includes vacuum tubes 1904 releasably connected to and in fluid communication with each of the suction cups 1814. The proximal ends (not shown) of the vacuum tubes 1904 may be connected to an vacuum source to selectively apply suction to the suction cups 1814. The pins 1816 are releasably connected to push/pull wires (not shown) extending through the vacuum tubes 1904 such that the pins may be remotely and selectively advanced and retracted by manipulating the proximal ands of the push/pull wires.

Figure 20C:
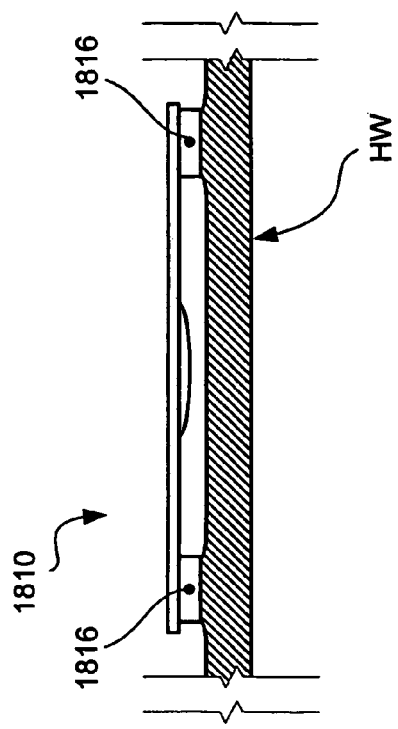
Figure 20D:
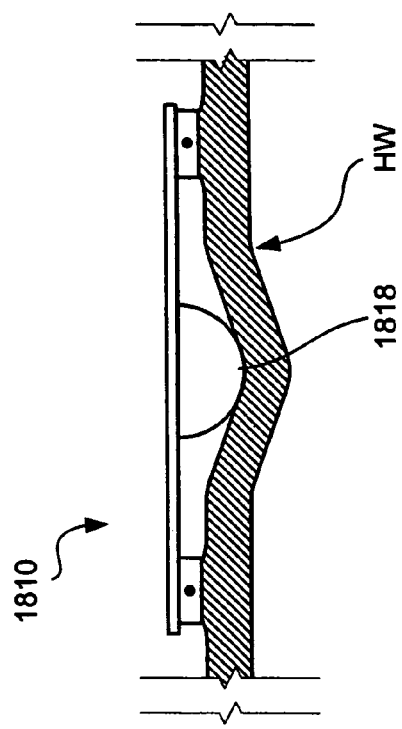
Figure 20A:
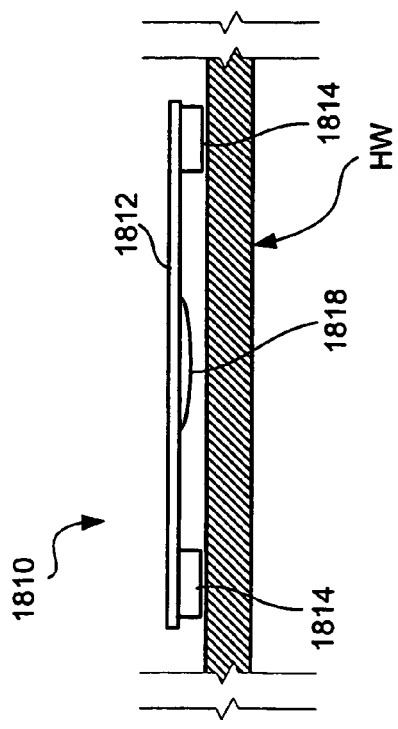

In FIGS. 20A-20D, an example of a method of deploying the space filling device 1810 is schematically shown. The space filling device 1810 may be positioned adjacent the heart wall HW (e.g., between the epicardium and pericardium) as shown in FIG. 20A, using delivery catheter 1900 (not shown) advanced over guide wire 2320 (shown in FIGS. 23A and 23B), by a transthoracic approach, for example. The balloon 1818 of space filling device 1810 may be positioned adjacent the MV or a specific part thereof (e.g., annulus AN or papillary muscles PM) as confirmed using by echocardiography, with the suction cups 1814 avoiding coronary vasculature as confirmed by radiography. For example, the balloon 1818 may be positioned adjacent the annulus and/or posterior papillary muscle PPM, with the suction cups 1814 disposed on opposite sides of the second and third obtuse marginals, such that the device 1810 is inferior of the circumflex artery CFX and straddles the second and third obtuse marginals.

Figure 20B:
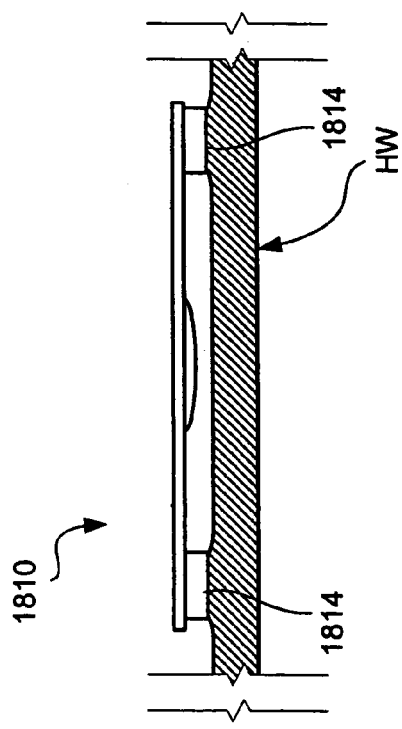

Suction is applied to the suction cups 1814 by vacuum tubes 1904 (not shown), causing a portion of the heart wall HW to be displaced into the interior of each suction cup 1814 as shown in FIG. 20B. Pins 1816 may then be advanced through the vacuum tubes 1904 and into each of the suction cups 1814 by remotely pushing on the push/pull wires, thus causing the pins 1816 to pierce the portion of the heart wall HW displaced into the interior of the suction cups 1814 as shown in FIG. 20C. The vacuum source may then be deactivated to release the vacuum applied to the suction cups 1814 via vacuum tubes 1904. Because the epicardium of the heart wall HW is a relatively tough tissue, the pins 1816 provide a secure connection to the heart wall HW. As an alternative, the pericardium may be suctioned into the suction cups 1814 such that the pins 1816 pierce the pericardium as well. The balloon 1818 may then be inflated as shown in FIG. 20D, and the desired acute effect may be confirmed by echocardiography. The catheter 1900 may then be disconnected from the space filling device 1810, leaving the balloon 1818 inflated and the pins 1816 secured to the heart wall HW in suction cups 1814.

Figure 21B:
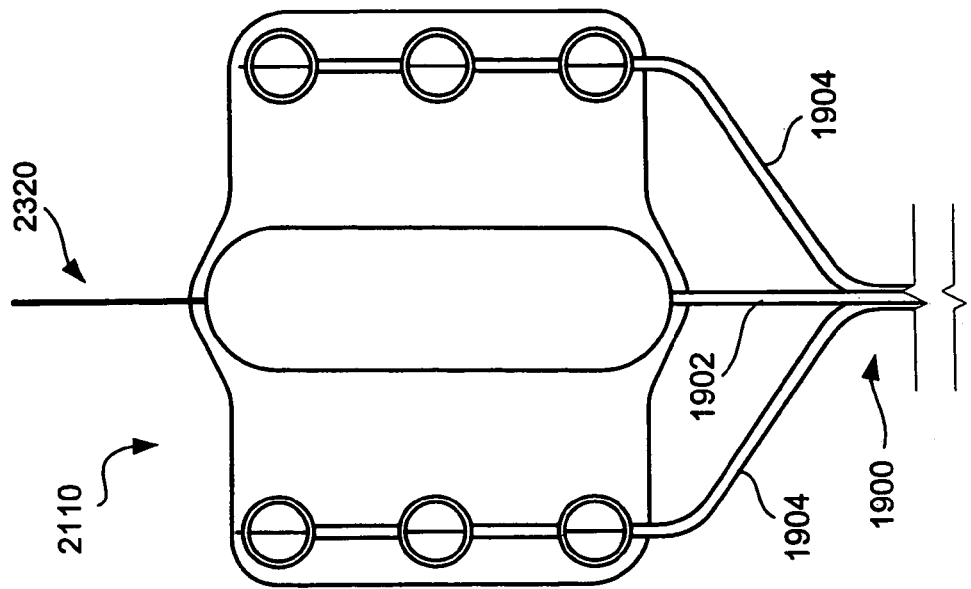
Figure 21A:
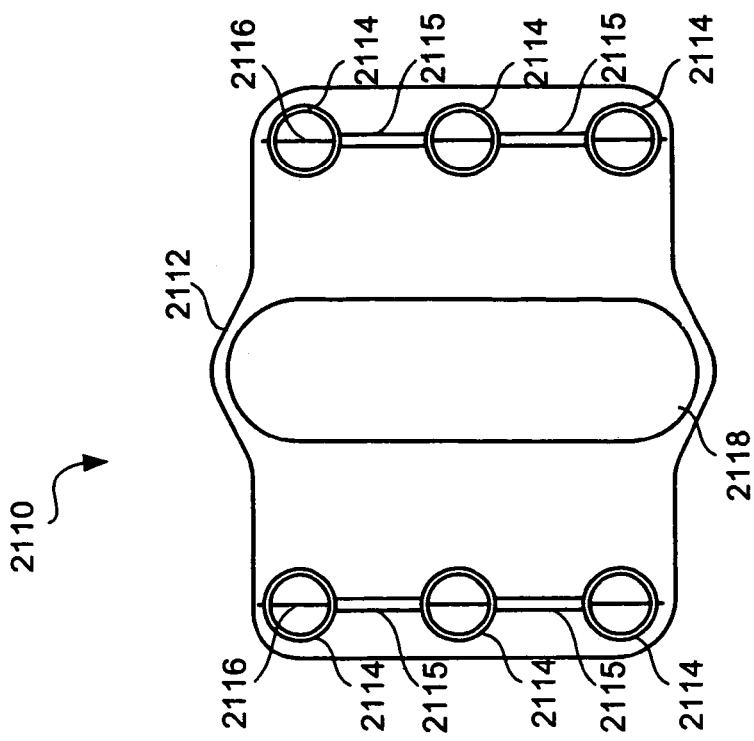

In FIG. 21A, a bottom view is shown of an alternative space filling device 2110, which may be similar in design and substantially the same in use as space filling device 1810 described previously. In this alternative embodiment, space filling device 2110 includes a base 2110 which may comprise, for example, a flexible polymer sheet having resistance to elongation. Two series of three suction cups 2114 each are uniformly distributed along and connected to opposite sides of the base 2112, and are interconnected by tubes 2115. A pin 2116 extends through and across each series of the suction cups 2114 and tubes 2115. A inflatable and deflatable balloon 2118 is connected to and extends from the bottom of the base 2112, and may be filled with a variety of materials as described previously. As compared to the space filling device 1810 described with reference to FIGS. 18A and 18B, the space filling device 2110 illustrated in FIG. 21A utilizes a balloon 2118 having a larger surface area and different geometry, and more suction cups 2114 interconnected by tubes 2115. As shown in FIG. 21B, delivery catheter 1900 may be connected to space filling device 2110 in a similar manner as the connection to space filling device 1810 described previously. Further, the steps of deploying space filling device 2110 may be the same as described previously for space filling device 1810.

With reference to FIGS. 22A-22C, various design alternatives for the suction cups 1814/2114 are shown as top views and side views. In FIG. 22A, the suction cup 2200 includes a circular wall portion 2202 defining an interior with an open bottom and top. A pin 2204 extends through holes in the wall 2202 as well as the interior defined by circular wall 2202. With an open bottom and top, suction applied to the cup 2200 pulls both the heart wall (at least the epicardium) and the pericardium into the interior allowing the pin 2204 to pierce through both tissue layers.

In FIG. 22B, the suction cup 2210 includes a circular wall portion 2212 defining an interior. A cap 2216 covers the top portion of the wall 2212 to define a closed top portion and an open bottom potion of the cup 2210. A pin 2214 extends through holes in the wall 2212 as well as the interior defined by circular wall 2212. With an open bottom and a closed top, suction applied to the cup 2210 pulls the heart wall (at least the epicardium) into the interior while the cover 2216 prevents the pericardium from entering, thus allowing the pin 2214 to pierce through the heart wall but not the pericardium.

In FIG. 22B, the suction cup 2220 includes a circular wall portion 2222 defining an interior. A series of crossing wires 2226 cover the top portion of the wall 2222 to define a screened top portion and an open bottom potion of the cup 2220. The wall 2222 may be formed of a tubular structure with a highly elastic wire (e.g., NiTi) running therethrough, and the wires 2226 may be formed of a highly elastic material (e.g., NiTi) such that the entire cup 2220 may be collapsed into a delivery configuration small enough to fit into a delivery catheter and subsequently deployed into an expanded configuration as shown. A pin 2224 extends through holes in the wall 2222 as well as the interior defined by the wall 2222. With an open bottom and a screened top, suction applied to the cup 2220 pulls the heart wall (at least the epicardium) into the interior. Depending on the density of wires 2226 and the amount of suction applied, the pericardium may be selectively pulled into the interior, thus allowing the pin 2224 to pierce through the heart wall and optionally the pericardium.

With reference to FIG. 22D, an alternative implantation arrangement is shown. In this embodiment, three or more suction cups 2220 are attached to the heart wall and pericardium to isolate and hold the balloon 2218 therebetween. By connecting to both the epicardium and the heart wall in three or more locations, the balloon 2218 is constrained by the heart wall, the epicardium and the suction cup anchors 2220. This arrangement eliminates the need to interconnect the balloon 2218 and suction cups 2220 (e.g., by a base structure), and permits the suction cups and balloon to be separately delivered in a smaller profile enabling transluminal delivery through a catheter.

Conclusion

From the foregoing, it will be apparent to those skilled in the art that the present invention provides, in exemplary no-limiting embodiments, devices and methods for improving the function of a valve (e.g., mitral valve) by positioning a spacing filling device outside and adjacent the heart wall such that the device applies an inward force against the heart wall acting on the valve. The device may be remotely secured to the heart wall. A substantially equal and opposite force may be provided by securing the device to the heart wall, and/or a substantially equal and opposite outward force may be applied against anatomical structure outside the heart wall. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What claimed is:

1. A method for improving heart valve function, the method comprising:
   providing a device comprising at least one expandable protrusion; and
   positioning the expandable protrusion in contact with an external surface of the heart wall such that the protrusion exerts an inward force against the heart wall proximate a valve, wherein the force is sufficient to alter valve function and draw leaflets of the valve together, and wherein the valve leaflets define a line of coaptation and positioning the expandable protrusion includes positioning the expandable protrusion such that the inward force is exerted substantially orthogonal to the line of coaptation.

2. The method of claim 1, further comprising positioning the device such that the device exerts a force substantially opposite to the inward force as a result of securing the device to the heart wall.

3. The method of claim 1, further comprising positioning the device such that the device exerts a force substantially opposite to the inward force on anatomical structure external to the heart wall.

4. The method of claim 1, wherein the valve is a mitral valve.

5. The method of claim 1, further comprising adjusting a position of the device while observing the valve function.

6. The method of claim 1, wherein the inward force is exerted on an annulus of the valve.

7. The method of claim 1, wherein the inward force is sufficient to reposition papillary muscles of the valve.

8. The method of claim 1, further comprising positioning the device outside an epicardium of the heart.

9. The method of claim 8, further comprising positioning the device between the epicardium and a pericardium of the heart.

10. The method of claim 9, further comprising attaching the device to the epicardium.

11. The method of claim 10, further comprising maintaining the device free of the pericardium.

12. The method of claim 1, further comprising delivering the device to the heart via a surgical approach.

13. The method of claim 2, wherein the force exerted substantially opposite the inward force is substantially equal to the inward force.

14. The method of claim 3, wherein the force exerted substantially opposite the inward force is substantially equal to the inward force.

15. The method of claim 1, wherein the inward force is exerted throughout the cardiac cycle.

16. A method for improving heart valve function, the method comprising:
   providing a device having at least one protrusion; and
   positioning the device relative to the heart such that the at least one protrusion is in contact with an external surface of a heart wall and exerts an inward force against the heart wall proximate the valve and such that the device exerts a force substantially opposite to the inward force against an anatomical structure outside the heart wall, wherein the inward force is sufficient to draw leaflets of the valve together, and wherein the valve leaflets define a line of coaptation and positioning the protrusion includes positioning the protrusion such that the inward force is exerted substantially orthogonal to the line of coaptation.

17. The method of claim 16, wherein the at least one protrusion exerts an inward force sufficient to alter valve function.

18. The method of claim 16, wherein the valve is a mitral valve.

19. The method of claim 16, further comprising adjusting a position of the device while observing the valve function.

20. The method of claim 16, wherein the inward force is exerted on an annulus of the valve.

21. The method of claim 16, wherein the inward force is sufficient to reposition papillary muscles of the valve.

22. The method of claim 16, further comprising positioning the device outside an epicardium of the heart.

23. The method of claim 22, further comprising positioning the device between the epicardium and a pericardium of the heart.

24. The method of claim 23, further comprising attaching the device to the epicardium.

25. The method of claim 24, further comprising maintaining the device free of the pericardium.

26. The method of claim 16, further comprising delivering the device to the heart via a surgical approach.

27. The method of claim 16, wherein the force exerted substantially opposite the inward force is substantially equal to the inward force.

28. The method of claim 16, wherein the inward force is exerted throughout the cardiac cycle.

29. A method for treating a heart valve, comprising
   providing a passive external heart device having a balloon and an elongate base;
   positioning the external heart device adjacent the heart valve;
   securing the external heart device to an external surface of a patient's heart; and
   adjusting a size of the balloon to apply a force on the heart valve, throughout a cardiac cycle, wherein positioning the external heart device adjacent the heart valve includes positioning the external heart device adjacent an atrioventricular groove.

30. The method of claim 29, wherein no portion of the external heart device is placed within a chamber of the patient's heart.

31. The method of claim 29, wherein the heart valve is a mitral valve.

32. The method of claim 29, wherein adjusting a size of the balloon includes inflating the balloon.

33. The method of claim 29, further comprising the step of monitoring an effect of the external heart device on the heart valve.

34. The method of claim 29, further comprising the step of positioning the external heart device between an external heart wall and a pericardium.

35. The method of claim 29, wherein securing the external heart device to an external surface of the patient's heart includes piercing an external wall of the patient's heart.

36. The method of claim 29, wherein the external heart device surrounds a portion of the patient's heart.

37. A method of adjusting heart valve function, comprising:
   providing a passive external heart device having a chamber and an elongate base;
   positioning the external heart device adjacent the heart valve and proximate an atrioventricular groove;
   securing the external heart device to an external surface of a patient's heart, such that the chamber is disposed between a heart wall and the elongate base;
   adjusting a size of the chamber to apply a force on the heart wall, throughout a cardiac cycle; and
   monitoring an effect of the external heart device on the heart valve.

38. A method for improving heart valve function, the method comprising:
   providing a device comprising at least one expandable protrusion;
   positioning the expandable protrusion in contact with an external surface of the heart wall such that the protrusion exerts an inward force against the heart wall proximate a valve, wherein the force is sufficient to alter valve function; and
   positioning the device outside an epicardium of the heart.

39. The method of claim 38, further comprising positioning the device between the epicardium and a pericardium of the heart.

40. The method of claim 39, further comprising attaching the device to the epicardium.

41. The method of claim 40, further comprising maintaining the device free of the pericardium.

42. A method for improving heart valve function, the method comprising:
   providing a device having at least one protrusion;
   positioning the device relative to the heart such that the at least one protrusion is in contact with an external surface of a heart wall and exerts an inward force against the heart wall proximate the valve and such that the device exerts a force substantially opposite to the inward force against an anatomical structure outside the heart wall; and
   positioning the device outside an epicardium of the heart.

43. The method of claim 42, further comprising positioning the device between the epicardium and a pericardium of the heart.

44. The method of claim 43, further comprising attaching the device to the epicardium.

45. The method of claim 44, further comprising maintaining the device free of the pericardium.

46. A method for treating a heart valve, comprising
   providing a passive external heart device having a balloon and an elongate base;
   positioning the external heart device adjacent the heart valve;
   securing the external heart device to an external surface of a patient's heart;
   adjusting a size of the balloon to apply a force on the heart valve, throughout a cardiac cycle; and
   positioning the external heart device between an external heart wall and a pericardium.

47. A method for treating a heart valve, comprising
   providing a passive external heart device having a balloon and an elongate base;
   positioning the external heart device adjacent the heart valve;
   securing the external heart device to an external surface of a patient's heart; and
   adjusting a size of the balloon to apply a force on the heart valve, throughout a cardiac cycle, wherein securing the external heart device to an external surface of the patient's heart includes piercing an external wall of the patient's heart.

* * * * *

UNITED STATES PATENT AND TRADEMARK OFFICE
CERTIFICATE OF CORRECTION

PATENT NO. : 7,666,224 B2
APPLICATION NO. : 11/175270
DATED : February 23, 2010
INVENTOR(S) : Vidlund et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1265 days.

Signed and Sealed this

Seventh Day of December, 2010

David J. Kappos
*Director of the United States Patent and Trademark Office*